United States Patent
Jin et al.

(10) Patent No.: US 11,457,894 B2
(45) Date of Patent: Oct. 4, 2022

(54) WIRELESS ULTRASOUND PROBE USING WIRELESSLY SUPPLIED POWER, ULTRASOUND DIAGNOSIS APPARATUS WIRELESSLY CONNECTED TO WIRELESS ULTRASOUND PROBE, OPERATING METHOD OF ULTRASOUND DIAGNOSIS APPARATUS, AND OPERATING METHOD OF WIRELESS ULTRASOUND PROBE

(71) Applicant: SAMSUNG MEDISON CO., LTD., Gangwon-do (KR)

(72) Inventors: Gil-Ju Jin, Seoul (KR); Mi-Jeoung Ahn, Seoul (KR)

(73) Assignee: SAMSUNG MEDISON CO., LTD., Ganwon-Do (KR)

(*) Notice: Subject to any disclaimer, the term of this patent is extended or adjusted under 35 U.S.C. 154(b) by 304 days.

(21) Appl. No.: 16/688,564

(22) Filed: Nov. 19, 2019

(65) Prior Publication Data
US 2020/0100767 A1 Apr. 2, 2020

Related U.S. Application Data

(62) Division of application No. 14/263,675, filed on Apr. 28, 2014, now Pat. No. 10,575,824.

(30) Foreign Application Priority Data

Apr. 29, 2013 (KR) .................. 10-2013-0047696
Jun. 28, 2013 (KR) .................. 10-2013-0075947

(51) Int. Cl.
*A61B 8/00* (2006.01)
*H02J 50/15* (2016.01)
(Continued)

(52) U.S. Cl.
CPC ............ *A61B 8/467* (2013.01); *A61B 8/4472* (2013.01); *A61B 8/462* (2013.01); *A61B 8/54* (2013.01);
(Continued)

(58) Field of Classification Search
CPC ....... A61B 8/467; A61B 8/4472; A61B 8/462; A61B 8/4405; A61B 8/4433; A61B 8/565
See application file for complete search history.

(56) References Cited

U.S. PATENT DOCUMENTS 6,798,716 B1 9/2004 Charych
10,105,124 B2 10/2018 Tashiro
(Continued)

FOREIGN PATENT DOCUMENTS

JP 2008-018109 A 1/2008
JP 2010-179052 A 8/2010
(Continued)

OTHER PUBLICATIONS

Korean Notice of Allowance dated Jul. 24, 2020 issued Korean Patent Application No. 10-2013-0047696 (with English translation).
(Continued)

*Primary Examiner* — Joel F Brutus
(74) *Attorney, Agent, or Firm* — Morgan, Lewis & Bockius LLP

(57) ABSTRACT

Provided are an ultrasound probe and an operating method of the ultrasound probe which can select a power transmission channel and/or a wireless power transmission mode that are most appropriate in an environment in which power transmission channels exist. The operating method of the ultrasound probe includes operations of obtaining a plurality of pieces of information about power transmission channels; displaying a power transmission channel list, based on the plurality of pieces of information about the power transmis-
(Continued)

sion channels; selecting a power transmission channel from the power transmission channel list; and receiving wireless power that is transmitted via the selected power transmission channel.

21 Claims, 15 Drawing Sheets

(51) Int. Cl.
  *H02J 50/12* (2016.01)
  *H02J 50/40* (2016.01)
  *H02J 50/80* (2016.01)
(52) U.S. Cl.
  CPC ............... *A61B 8/56* (2013.01); *A61B 8/565* (2013.01); *H02J 50/12* (2016.02); *H02J 50/15* (2016.02); *H02J 50/40* (2016.02); *H02J 50/80* (2016.02); *A61B 8/4405* (2013.01); *A61B 8/4411* (2013.01); *A61B 8/4433* (2013.01); *A61B 8/465* (2013.01)

(56) References Cited

U.S. PATENT DOCUMENTS

| | | |
|---|---|---|
| 2009/0112099 A1 | 4/2009 | Kurokawa |
| 2010/0185096 A1 | 7/2010 | Miyachi et al. |
| 2012/0197124 A1 | 8/2012 | Nakamura |
| 2013/0076306 A1 | 3/2013 | Lee et al. |
| 2013/0084800 A1 | 4/2013 | Troberg et al. |

FOREIGN PATENT DOCUMENTS

| | | |
|---|---|---|
| JP | 2010-233826 A | 10/2010 |
| JP | 2011000236 A | 1/2011 |
| JP | 4785572 B2 | 10/2011 |
| JP | 2012-075866 A | 4/2012 |
| WO | 2011/156815 A1 | 12/2011 |

OTHER PUBLICATIONS

Korean Notice of Allowance dated Jul. 22, 2020 issued Korean Patent Application No. 10-2013-0075947 (with English translation).
Korean Office Action dated May 26, 2020 issued Korean Patent Application No. 10-2013-0047696 (with English translation).
Korean Office Action dated Nov. 19, 2019 issued in Korean Patent Application No. 10-2013-0047696 (with English translation).
Korean Office Action dated Jan. 17, 2020 issued in Korean Patent Application No. 10-2013-0075947 (with English translation).
Extended European Search Report issued in European Application No. 14161466.9 dated Oct. 27, 2014, 7 pages.
U.S. Notice of Allowance dated Aug. 1, 2019 issued in U.S. Appl. No. 14/263,675.
U.S. Non-Final Office Action dated Apr. 18, 2019 issued in U.S. Appl. No. 14/263,675.
U.S. Final Office Action dated Nov. 16, 2018 issued in U.S. Appl. No. 14/263,675.
U.S. Non-Final Office Action dated Jun. 4, 2018 issued in U.S. Appl. No. 14/263,675.
U.S. Non-Final Office Action dated Mar. 13, 2017 issued in U.S. Appl. No. 14/263,675.

(a)

(b)

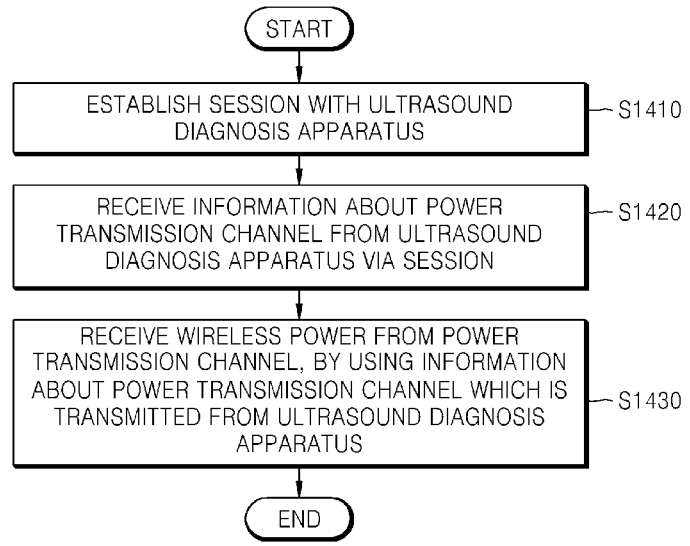
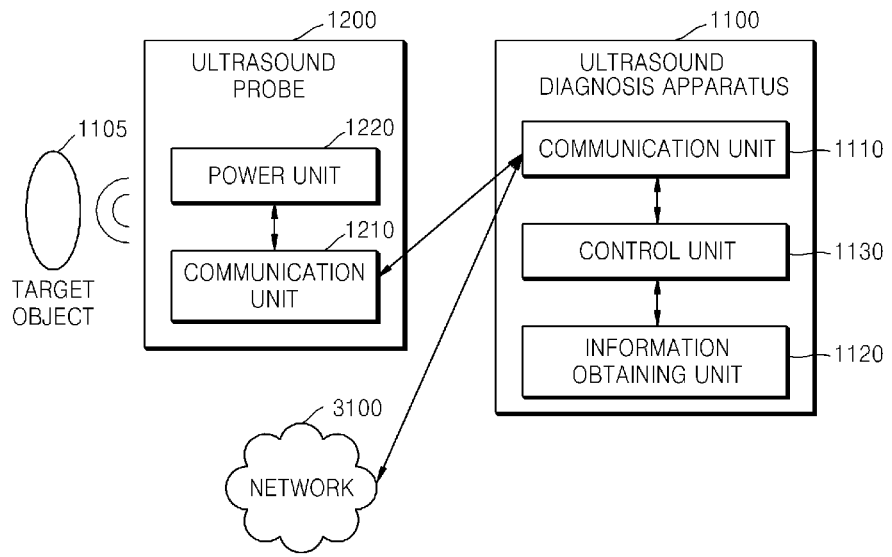

WIRELESS ULTRASOUND PROBE USING WIRELESSLY SUPPLIED POWER, ULTRASOUND DIAGNOSIS APPARATUS WIRELESSLY CONNECTED TO WIRELESS ULTRASOUND PROBE, OPERATING METHOD OF ULTRASOUND DIAGNOSIS APPARATUS, AND OPERATING METHOD OF WIRELESS ULTRASOUND PROBE

CROSS-REFERENCE TO RELATED PATENT APPLICATIONS

This application is a divisional patent application of U.S. patent application Ser. No. 14/263,675, filed on Apr. 28, 2014, which claims the benefit of Korean Patent Application Nos. 10-2013-0047696, filed on Apr. 29, 2013, and 10-2013-0075947, filed on Jun. 28, 2013, in the Korean Intellectual Property Office, the disclosures of which are incorporated herein in their entireties by reference.

BACKGROUND OF THE INVENTION

1. Field of the Invention

The present invention relates to an ultrasound diagnosis apparatus, an ultrasound probe, an operating method of the ultrasound diagnosis apparatus, and an operating method of the ultrasound probe, and more particularly, to a wireless ultrasound probe that operates by using wirelessly supplied power, an operating method of the wireless ultrasound probe, an ultrasound diagnosis apparatus that communicates with the ultrasound probe, and an operating method of the ultrasound diagnosis apparatus.

2. Description of the Related Art

An ultrasound system delivers an ultrasound signal, which is generated at a transducer of an ultrasound probe, to a predetermined internal part of a target object, and obtains an image of the internal part of the target object by receiving information of an echo signal reflected from the internal part of the target object. In particular, the ultrasound system is used for medical purposes including observation, detection of foreign materials, damage measurement, or the like that are related to the internal part of the target object.

Compared to a diagnosis apparatus using X-rays, the ultrasound system is stable, displays an image in real-time, and is safe without a risk of radioactivity, and thus the ultrasound system is widely used with an image diagnosis apparatus.

Here, when a user obtains the image of the target object by using the ultrasound probe, the user is inconvenienced due to a communication cable that connects the ultrasound probe and an ultrasound diagnosis apparatus. In order to improve an operability of the ultrasound probe by resolving the inconvenience, it is required to arrange a wireless ultrasound probe that connects to the ultrasound diagnosis apparatus via wireless communication.

However, in the case of a wireless ultrasound probe having a battery that is charged while the wireless ultrasound probe is connected to or contacts a predetermined power supply unit (not shown), a user cannot use the wireless ultrasound probe while the battery is being charged. Thus, in order to solve the problem, wireless power may be supplied to the wireless ultrasound probe via a wireless power supply channel.

Here, in the case of an ultrasound system capable of providing an ultrasound image in real-time to a user, it is required to stably drive the wireless ultrasound probe that transmits data of the ultrasound image. Thus, in order to stably drive the wireless ultrasound probe, it is required to select a power transmission channel and/or a wireless power transmission mode that are most appropriate in an environment in which power transmission channels exist.

SUMMARY OF THE INVENTION

One or more embodiments of the present invention include a wireless ultrasound probe capable of selecting at least one power transmission channel from among power transmission channels that wirelessly supply a power, and an operating method of the wireless ultrasound probe.

One or more embodiments of the present invention include a wireless ultrasound probe capable of efficiently delivering user-required information by displaying information about each of power transmission channels that wirelessly supply a power, and an operating method of the wireless ultrasound probe.

One or more embodiments of the present invention include a wireless ultrasound probe capable of selecting the most appropriate power transmission channel and/or wireless power transmission mode in an environment where power transmission channels exist, by receiving a wireless power from a wireless power transmission channel that is selected by an ultrasound diagnosis apparatus and then by being charged with the wireless power.

One or more embodiments of the present invention include a wireless ultrasound probe capable of stably receiving a power by receiving a wireless power from a wireless power transmission channel and then by being charged with the wireless power, according to a control signal transmitted from an ultrasound diagnosis apparatus.

Additional aspects will be set forth in part in the description which follows and, in part, will be apparent from the description, or may be learned by practice of the presented embodiments.

According to one or more embodiments of the present invention, an operating method of an ultrasound probe includes operations of obtaining a plurality of pieces of information about power transmission channels, respectively; displaying a power transmission channel list, based on the plurality of pieces of information about the power transmission channels; selecting a power transmission channel from the power transmission channel list; and receiving wireless power that is transmitted via the selected power transmission channel.

The power transmission channel list may list at least some of the plurality of pieces of information about the power transmission channels, based on a priority order of the power transmission channels.

The operation of selecting the power transmission channel may be performed based on a user input that involves selecting the power transmission channel from the power transmission channel list.

The power transmission channel list may include information about a wireless power transmission mode by which the power transmission channels transmit wireless power to the ultrasound probe.

The wireless power transmission mode may include at least one of an electromagnetic induction method, an electromagnetic radiation method, an electromagnetic resonance method, and a wireless power transmission mode using an ultrasound.

The operation of obtaining the plurality of pieces of information may include operations of sensing a characteristic value of wireless power that is transmitted by each of the power transmission channels; and obtaining the characteristic value as each of the plurality of pieces of information about the power transmission channels, and wherein the characteristic value includes a value of at least one of a voltage, a current, and a frequency of the wireless power that is transmitted by each of the power transmission channels.

The operation of obtaining the plurality of pieces of information may include operations of receiving data signals that are transmitted by the power transmission channels, respectively; and obtaining the plurality of pieces of information about the power transmission channels, wherein the plurality of pieces of information about the power transmission channels are included in the data signals, respectively, and wherein each of the plurality of pieces of information about the power transmission channels includes a value of at least one of a voltage, a current, and a frequency of the wireless power that is transmitted by each of the power transmission channels.

The operating method may further include an operation of converting the wireless power, based on a rated voltage and a rated current of the ultrasound probe.

When the operation of receiving the wireless power that is transmitted via the selected power transmission channel is discontinued, the operating method may further include an operation of providing information indicating that the operation of receiving the wireless power is discontinued.

When the operation of receiving the wireless power that is transmitted via the selected power transmission channel is discontinued, the operating method may further include an operation of receiving wireless power that is transmitted via another power transmission channel.

At least one of the power transmission channels may correspond to one or more ultrasound diagnosis apparatuses.

The operating method may further include operations of charging a battery by using the wireless power; and generating ultrasound image data from an echo signal of an ultrasound signal that is transmitted to a target object, by using only a predetermined percentage of power that is charged in the battery, wherein the predetermined percentage of the power is determined based on a user input.

According to one or more embodiments of the present invention, an ultrasound probe may include an information obtaining unit for obtaining a plurality of pieces of information about power transmission channels; a display unit for displaying a power transmission channel list, based on the plurality of pieces of information about the power transmission channels; a control unit for selecting a power transmission channel from the power transmission channel list; and a power unit for receiving wireless power that is transmitted via the selected power transmission channel.

The power transmission channel list may list at least some of the plurality of pieces of information about the power transmission channels, based on a priority order of the power transmission channels.

The ultrasound probe may further include a user input unit for receiving an input that involves selecting the power transmission channel from the power transmission channel list, and the control unit may select the power transmission channel based on the input.

The power transmission channel list may include information about a wireless power transmission mode by which the power transmission channels transmit wireless power to the ultrasound probe.

The wireless power transmission mode may include at least one of an electromagnetic induction method, an electromagnetic radiation method, an electromagnetic resonance method, and a wireless power transmission mode using an ultrasound.

The information obtaining unit may sense a characteristic value of wireless power that is transmitted by each of the power transmission channels, and may obtain the characteristic value as each of the plurality of pieces of information about the power transmission channels, and the characteristic value may include a value of at least one of a voltage, a current, and a frequency of the wireless power that is transmitted by each of the power transmission channels.

The information obtaining unit may receive data signals that are transmitted by the power transmission channels, respectively, and may obtain the plurality of pieces of information about the power transmission channels, wherein the plurality of pieces of information about the power transmission channels are included in the data signals, respectively, and wherein each of the plurality of pieces of information about the power transmission channels includes a value of at least one of a voltage, a current, and a frequency of the wireless power that is transmitted by each of the power transmission channels.

The ultrasound probe may further include a power converting unit for converting the wireless power, based on a rated voltage and a rated current of the ultrasound probe.

When the operation of receiving the wireless power that is transmitted via the selected power transmission channel is discontinued, the control unit may control the display unit to provide information indicating that the receiving of the wireless power is discontinued.

When the operation of receiving the wireless power that is transmitted via the selected power transmission channel is discontinued, the control unit may control the power unit to receive wireless power that is transmitted via another power transmission channel.

At least one of the power transmission channels may correspond to one or more ultrasound diagnosis apparatuses.

The ultrasound probe may further include an image generating unit for generating ultrasound image data from an echo signal of an ultrasound signal that is transmitted to a target object, and the power unit may include a battery that is charged due to the wireless power, the control unit may control the power unit to supply only a predetermined percentage of power that is charged in the battery, to the image generating unit, and the predetermined percentage of the power may be determined based on a user input.

According to one or more embodiments of the present invention, a non-transitory computer-readable recording medium includes a recorded program for executing the operating method, by using a computer.

According to one or more embodiments of the present invention, an operating method of an ultrasound diagnosis apparatus includes operations of establishing a session with an ultrasound probe; obtaining a plurality of pieces of information about wireless power transmission channels, respectively; selecting a wireless power transmission channel from among the wireless power transmission channels, based on the plurality of pieces of information about the wireless power transmission channels; and transmitting information about the selected wireless power transmission channel to the ultrasound probe via the session.

The information about the selected wireless power transmission channel may include information to be used by the ultrasound probe so as to receive a wireless power from the selected wireless power transmission channel.

The information about the selected wireless power transmission channel may include at least one of an identifier of the selected wireless power transmission channel, a characteristic value of a wireless power transmitted by the selected wireless power transmission channel, and a wireless power transmission mode used by the selected wireless power transmission channel so as to transmit the wireless power.

The information about the selected wireless power transmission channel may be transmitted to the ultrasound probe when the ultrasound diagnosis apparatus is booted up or starts receiving a wireless power from the selected wireless power transmission channel.

The operation of transmitting the information may include an operation of obtaining information about a remaining power of a battery of the ultrasound probe; and when a value of the remaining power is equal to or less than a predetermined value, an operation of transmitting a control signal to the ultrasound probe so as to control the ultrasound probe to receive a wireless power from the selected wireless power transmission channel.

The operation of selecting the wireless power transmission channel may include operations of obtaining information about a wireless power that is receivable by the ultrasound probe; and selecting the wireless power transmission channel from among the wireless power transmission channels, based on the plurality of pieces of information about the wireless power transmission channels, and the information about the wireless power that is receivable by the ultrasound probe.

The information about the wireless power that is receivable by the ultrasound probe may include at least one of information about a characteristic value of the wireless power that is receivable by the ultrasound probe, and information about a wireless power transmission mode by which the ultrasound probe receives the wireless power, and the characteristic value of the wireless power may indicate at least one of a voltage, a current, a power, and a frequency of the wireless power.

The operation of selecting the wireless power transmission channel may include an operation of selecting the wireless power transmission channel from among the wireless power transmission channels, based on priority orders of the wireless power transmission channels.

The operation of selecting the wireless power transmission channel may include operations of displaying a wireless power transmission channel list showing at least some of the plurality of pieces of information about the power transmission channels, based on the plurality of pieces of information about the power transmission channels; and selecting the wireless power transmission channel, based on a user input of selecting the wireless power transmission channel from the wireless power transmission channel list.

The wireless power transmission channel list may include at least one of a plurality of pieces of information about characteristic values of wireless powers that are transmittable from the wireless power transmission channels to the ultrasound probe, and a plurality of pieces of information about wireless power transmission modes by which the wireless power transmission channels transmit the wireless powers to the ultrasound probe, and each of the characteristic values of the wireless powers may indicate at least one of a voltage, a current, a power, and a frequency of each of the wireless powers.

According to one or more embodiments of the present invention, an operating method of an ultrasound probe includes operations of establishing a session with an ultrasound diagnosis apparatus; receiving information about a wireless power transmission channel from the ultrasound diagnosis apparatus via the session; and receiving a wireless power from the wireless power transmission channel, by using the information about the wireless power transmission channel received from the ultrasound diagnosis apparatus.

According to one or more embodiments of the present invention, an ultrasound diagnosis apparatus includes a communication unit for establishing a session with an ultrasound probe; an information obtaining unit for obtaining a plurality of pieces of information about wireless power transmission channels, respectively; and a control unit for selecting a wireless power transmission channel from among the wireless power transmission channels, based on the plurality of pieces of information about the wireless power transmission channels, wherein the communication unit transmits information about the selected wireless power transmission channel to the ultrasound probe via the session.

The information about the selected wireless power transmission channel may include information to be used by the ultrasound probe so as to receive a wireless power from the selected wireless power transmission channel.

The information about the selected wireless power transmission channel may include at least one of an identifier of the selected wireless power transmission channel, a characteristic value of a wireless power transmitted by the selected wireless power transmission channel, and a wireless power transmission mode used by the selected wireless power transmission channel so as to transmit the wireless power.

The information about the selected wireless power transmission channel may be transmitted to the ultrasound probe when the ultrasound diagnosis apparatus is booted up or starts receiving a wireless power from the selected wireless power transmission channel.

The information obtaining unit may further obtain information about a remaining power of a battery of the ultrasound probe, and when a value of the remaining power is equal to or less than a predetermined value, the control unit may transmit a control signal to the ultrasound probe so as to control the ultrasound probe to receive a wireless power from the selected wireless power transmission channel.

The information obtaining unit may further obtain information about a wireless power that is receivable by the ultrasound probe, and the control unit may select the wireless power transmission channel from among the wireless power transmission channels, based on the plurality of pieces of information about the wireless power transmission channels, and the information about the wireless power that is receivable by the ultrasound probe.

The information about the wireless power that is receivable by the ultrasound probe may include at least one of information about a characteristic value of the wireless power that is receivable by the ultrasound probe, and information about a wireless power transmission mode by which the ultrasound probe receives the wireless power, and the characteristic value of the wireless power may indicate at least one of a voltage, current, a power, and a frequency of the wireless power.

The control unit may select the wireless power transmission channel from among the wireless power transmission channels, based on priority orders of the wireless power transmission channels.

The ultrasound diagnosis apparatus may further include a display unit for displaying a wireless power transmission channel list showing at least some of the plurality of pieces of information about the power transmission channels, based on the plurality of pieces of information about the power transmission channels; and a user input unit for receiving a user input of selecting the wireless power transmission channel from the wireless power transmission channel list, wherein the control unit selects the wireless power transmission channel, based on the user input.

The wireless power transmission channel list may include at least one of a plurality of pieces of information about characteristic values of wireless powers that are transmittable from the wireless power transmission channels to the ultrasound probe, and a plurality of pieces of information about wireless power transmission modes by which the wireless power transmission channels transmit the wireless powers to the ultrasound probe, and each of the characteristic values of the wireless powers may indicate at least one of a voltage, a current, a power, and a frequency of each of the wireless powers.

According to one or more embodiments of the present invention, an ultrasound probe includes a communication unit for establishing a session with an ultrasound diagnosis apparatus; a power unit for receiving a wireless power from a wireless power transmission channel via the session, by using information about the wireless power transmission channel received from the ultrasound diagnosis apparatus.

BRIEF DESCRIPTION OF THE DRAWINGS

The above and other features- and advantages of the present invention will become more apparent by describing in detail exemplary embodiments thereof with reference to the attached drawings in which:

FIG. 14 is a flowchart of an operating method of an ultrasound probe, according to another embodiment of the present invention;

FIGS. 15A and 15B are block diagrams illustrating an ultrasound probe and an ultrasound diagnosis apparatus, according to embodiments of the present invention.

DETAILED DESCRIPTION OF THE INVENTION

Figure 1:
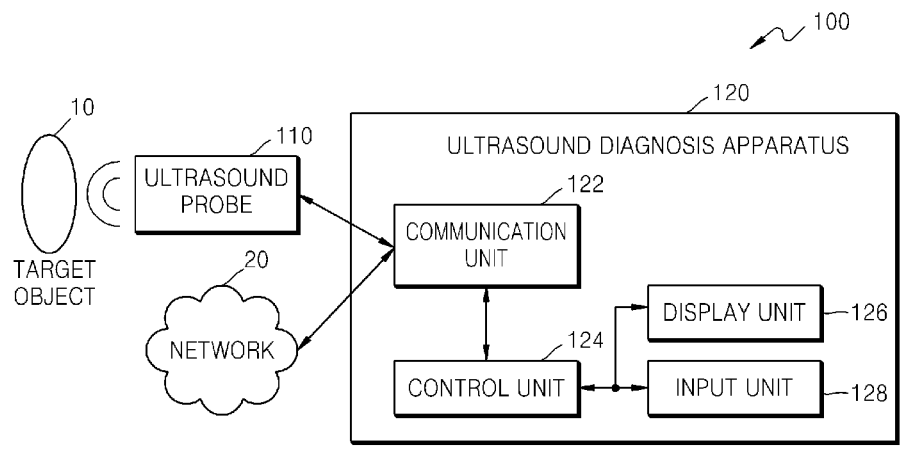
FIG. 1 is a block diagram of a general ultrasound system including a wireless ultrasound probe.

Hereinafter, the present invention will be described in detail by explaining exemplary embodiments of the invention with reference to the attached drawings. The invention may, however, be embodied in many different forms, and should not be construed as being limited to the embodiments set forth herein; rather, these embodiments are provided so that this disclosure will be thorough and complete, and will fully convey the concept of the invention to those skilled in the art. In the following description, well-known functions or constructions are not described in detail since they would obscure the invention with unnecessary detail, and like reference numerals in the drawings denote like or similar elements throughout the specification.

Throughout the specification, it will also be understood that when an element is referred to as being "connected to" another element, it can be directly connected to the other element, or intervening elements may also be present. Also, when a part "includes" or "comprises" an element, unless there is a particular description contrary thereto, the part can further include other elements, not excluding the other elements.

Throughout the specification, a term 'target object' may be a target inanimate object or a target animated object, which is displayed via an image. Also, the target object may be a part of a human body and may include the liver, the heart, the womb, the brain, the breast, the abdominal region, or the like, a fetus, or a cross-section of a part of a human body. Throughout the specification, a "user" may be a medical expert including a doctor, a nurse, a medical laboratory technologist, a sonographer, or the like.

Hereinafter, the present invention will be described in detail by explaining exemplary embodiments of the invention with reference to the attached drawings.

As used herein, the term "and/or" includes any and all combinations of one or more of the associated listed items. Expressions such as "at least one of," when preceding a list of elements, modify the entire list of elements and do not modify the individual elements of the list.

FIG. 1 is a block diagram of a general ultrasound system 100 including a wireless ultrasound probe 110.

The ultrasound system 100 may include the wireless ultrasound probe 110 and an ultrasound diagnosis apparatus 120.

The wireless ultrasound probe 110 may be wirelessly connected with the ultrasound diagnosis apparatus 120, so that the wireless ultrasound probe 110 may transmit an ultrasound signal to a target object 10 according to a control signal that is transmitted by the ultrasound diagnosis apparatus 120 and may generate a reception signal by receiving an ultrasound signal (e.g., an ultrasound echo signal) that is reflected from the target object 10. The wireless ultrasound probe 110 may generate ultrasound image data by focusing the reception signal and then may transmit the ultrasound image data to the ultrasound diagnosis apparatus 120.

The wireless ultrasound probe 110 generates pulses for generating a transmission ultrasound according to a pulse repetition frequency (PRF), in response to a control signal transmitted by the ultrasound diagnosis apparatus 120. The wireless ultrasound probe 110 applies a delay time for determining transmission directionality to the pulses. Each of the pulses having the delay time applied thereto corresponds to each of a plurality of piezoelectric vibrators included in a transducer. The wireless ultrasound probe 110 applies pulses to the piezoelectric vibrators, respectively, by timings that respectively correspond to the pulses having the delay time applied thereto.

The wireless ultrasound probe 110 may generate ultrasound data by processing an echo signal reflected from the target object 10. The wireless ultrasound probe 110 amplifies the echo signal for each channel and performs analog-to-digital conversion on the amplified echo signal. The wireless ultrasound probe 110 applies a delay time for determining reception directionality to the digitally converted echo signal, and then generates the ultrasound data by summing the echo signals having the delay time applied thereto.

The ultrasound diagnosis apparatus 120 may be wirelessly connected with the wireless ultrasound probe 110, so that the ultrasound diagnosis apparatus 120 may generate an ultrasound image by using the ultrasound image data transmitted by the wireless ultrasound probe 110, and may display the ultrasound image.

The ultrasound diagnosis apparatus 120 may include a communication unit 122, a control unit 124, a display unit 126, and an input unit 128.

The ultrasound diagnosis apparatus 120 may be embodied as a cart-type ultrasound diagnosis apparatus or a portable ultrasound diagnosis apparatus. The portable ultrasound diagnosis apparatus may include, but is not limited to, a Picture Archiving and Communication System (PACS) viewer, hand-carried cardiac ultrasound (HCU) equipment, a smartphone, a laptop computer, a personal digital assistant (PDA), and a tablet PC.

The communication unit 122 may perform wireless communication with the wireless ultrasound probe 110. The communication unit 122 may transmit the control signal from the control unit 124 to the wireless ultrasound probe 110, and may receive the ultrasound image data that is transmitted by the wireless ultrasound probe 110.

Also, the communication unit 122 may be wired or wirelessly connected with a network 20, thereby communicating with an external device or a server. The communication unit 122 may exchange data with a hospital server or other medical apparatuses in a hospital via a picture archiving and communication system (PACS). Also, the communication unit 122 may perform data communication according to the digital imaging and communications in medicine (DICOM) standard.

The communication unit 122 may transmit or receive data such as an ultrasound image, ultrasound data, Doppler data, or the like of the target object which are related to a diagnosis about the target object, and may transmit or receive a medical image captured by other medical apparatuses such as a computerized tomography (CT) apparatus, a magnetic resonance imaging (MRI) apparatus, an X-ray apparatus, or the like. Furthermore, the communication unit 122 may receive information such as a diagnosis history or a treatment schedule about a patient from the hospital server, and then may use the information in the diagnosis about the target object. In addition, the communication unit 122 may perform data communication with not only the hospital server or the other medical apparatuses in the hospital but also may perform data communication with a portable terminal operated by a doctor or a customer.

Examples of a short-distance wireless communication technology available to the communication unit 122 may include, but are not limited to, a wireless local area network (LAN), Wi-Fi, Bluetooth, ZigBee, Wi-Fi Direct (WFD), ultra wideband (UWB), infrared Data Association (IrDA), Bluetooth Low Energy (BLE), and Near Field Communication (NFC).

Examples of a wired communication technology available to the communication unit 122 may include a pair cable, a coaxial cable, an optical fiber cable, an Ethernet cable, etc.

By using a mobile communication technology available to the communication unit 122, the communication unit 122 exchanges a wireless signal with at least one of a base station, an external terminal, and a server in a mobile communication network. Here, the wireless signal may include various types of data due to transmitting and receiving a voice signal, a video call signal, or text/multimedia message.

The control unit 124 may generate control signals so as to control an operation of the wireless ultrasound probe 110 according to user-requested information that is provided via the input unit 128. The control signals may include a control signal that is used to control the wireless ultrasound probe 110 to generate an ultrasound signal, and a control signal that is used to control transmission and reception of the ultrasound signal. In addition, the control unit 124 may control wireless communication with the wireless ultrasound probe 110, and may control generation and display of an ultrasound image.

According to the user-requested information via the input unit 128, the control unit 124 may perform various signal processing operations (e.g., gain adjustment or the like) on the ultrasound image data, which is transmitted by the wireless ultrasound probe 110) so as to generate the ultrasound image. The control unit 124 may generate the ultrasound image that corresponds to the user-requested information, by using a signal-processed reception signal.

The control unit 124 may generate and display an ultrasound image by performing a scan conversion process on the ultrasound data received from the wireless ultrasound probe 110 via the communication unit 122. The control unit 124 may generate not only the ultrasound image in a gray scale but may also generate a Doppler image showing movement of the target object 10 according to an amplitude mode (hereinafter, the A mode), a brightness mode (hereinafter, the B mode), a motion mode (hereinafter, the M mode), and a Doppler mode (hereinafter, the D mode). The Doppler image may include a blood flow Doppler image (also called 'colour Doppler image') showing blood flow, a tissue Doppler image showing movement of tissue, and a spectral Doppler image indicating a movement speed of the target object 10 by using a waveform.

The display unit 126 may display the ultrasound image, which is generated by the control unit 124, on a screen.

The display unit 126 may display and output not only the ultrasound image but also various types of information processed by the ultrasound diagnosis apparatus 120, on a screen via a graphical user interface (GUI). In another embodiment, the ultrasound diagnosis apparatus 120 may include at least two display units 126.

The input unit 128 indicates a unit that receives an input of data for controlling the ultrasound diagnosis apparatus 120 from a user. The input unit 128 may include, but is not limited to, hardware elements such as a keypad, a mouse, a touch panel, a touch screen, a track ball, a jog switch, or the like, and thus may further include various input units such as an electrocardiogram measurement module, a breath measurement module, a voice recognition sensor, a gesture recognition sensor, a fingerprint recognition sensor, an iris recognition sensor, a depth sensor, a distance sensor, or the like.

The input unit 128 may generate the user-requested information in response to a user request. The user-requested information may include information on a user selection of at least one application out of a plurality of applications corresponding to diagnosis parts of the target object, information on a user selection about a diagnosis mode in which the ultrasound image is generated, information on a user adjustment of various gain values, or the like.

Although not illustrated in FIG. 1, the ultrasound diagnosis apparatus 120 may further include a memory (not shown).

The memory stores various types of information processed by the ultrasound diagnosis apparatus 120. For example, the memory may store medical data such as ultrasound data, an ultrasound image, etc. that are input/output and are related to a diagnosis of the target object 10, and may store an algorithm or a program to be executed in the ultrasound diagnosis apparatus 120.

The memory may be embodied as one of various types of storage mediums including a flash memory, a hard disk, an Electrically Erasable Programmable Read-Only Memory (EEPROM), etc. Also, the ultrasound diagnosis apparatus 120 may run a web storage or a cloud server that performs a storage function of the memory on the world wide web.

As illustrated in FIG. 1, the wireless ultrasound probe 110 that is wirelessly connected with the ultrasound diagnosis apparatus 120 requires a power supply method different from that of a wired ultrasound probe that receives a power from the ultrasound diagnosis apparatus 120 via a cable.

In the case of the wireless ultrasound probe 110 that operates by using only the power that is charged in an embedded battery, a user has a time limit in using the wireless ultrasound probe 110 due to a limit in capacity of the battery.

Also, in the case of the wireless ultrasound probe 110 in the battery is charged while the wireless ultrasound probe 110 is in contact with a predetermined power supply unit (not shown), the user cannot use the wireless ultrasound probe 110 while the battery is being charged.

Thus, one or more embodiments of the present invention provide an ultrasound probe 400 capable of solving the aforementioned problems by wirelessly receiving power, and an operating method of the ultrasound probe 400. Also, one or more embodiments of the present invention provide the ultrasound probe 400 capable of efficiently delivering information to a user, wherein the information is about a power transmission channel via which the power is wirelessly transmitted to the ultrasound probe 400, and an operating method of the ultrasound probe 400.

A method of wirelessly supplying electric energy may include an electromagnetic induction method based on electromagnetic induction that is generated due to a wireless power signal, an electromagnetic resonance method based on electromagnetic resonance that is generated due to a wireless power signal having a particular frequency, an electromagnetic radiation method (i.e., a non-radiation type wireless energy transmission method) based on electromagnetic radiation, a wireless power transmission mode (refer to U.S. Pat. No. 6,798,716 by Arthur Charych, which is about energy transmission using ultrasound), a wireless power transmission mode to be developed in the future, or the like. The ultrasound probe 400 may be supplied power by using at least one method of the aforementioned methods.

Also, one or more embodiments of the present invention provide the ultrasound probe 400 that provides a GUI for allowing a user to conveniently select a power transmission channel, by displaying a power transmission channel list based on information about each of power transmission channels capable of wirelessly supplying a power to the ultrasound probe 400. The ultrasound probe 400 and an operating method of the ultrasound probe 400 will be described in detail with reference to FIGS. 2 through 9.

In an environment in which power transmission channels exist, it is required for a wireless ultrasound probe to select a power transmission channel that is the most appropriate to the wireless ultrasound probe.

However, in general, an ultrasound probe may have a limited source, e.g., a limited processing speed of a processor or a limited capacity of a memory, compared to that of an ultrasound diagnosis apparatus. Also, the ultrasound probe may not include a display device or a user input device for receiving a user input of selecting a power transmission channel.

Thus, depending on specification of each of ultrasound probes, some of the ultrasound probes may not be capable of searching for the plurality of power transmission channels and then selecting the most appropriate power transmission channel from among the plurality of power transmission channels.

Also, an operation of searching for the plurality of power transmission channels and then selecting the most appropriate power transmission channel from among the plurality of power transmission channels may cause an overload to a corresponding ultrasound probe having a limited resource.

Therefore, an ultrasound diagnosis apparatus according to another embodiment of the present invention may reduce a load of an ultrasound probe by searching for power transmission channels and then selecting the most appropriate power transmission channel from among the plurality of power transmission channels.

Also, an ultrasound probe according to another embodiment of the present invention may receive and be charged with a wireless power from a wireless power transmission channel, in response to a control signal transmitted by an ultrasound diagnosis apparatus, so that user's inconvenience caused by separately charging the ultrasound probe is decreased. In addition, the ultrasound probe that may receive a wireless power and be charged with the wireless power by the ultrasound diagnosis apparatus, without a separate user input, may be automatically charged in consideration of a remaining power in the ultrasound probe, so that the ultrasound probe may stably operate at a user desired time.

In this regard, the ultrasound probe and an operating method of the ultrasound probe according to the other embodiments will be described in detail with reference to FIGS. 10 through 16.

Figure 2:
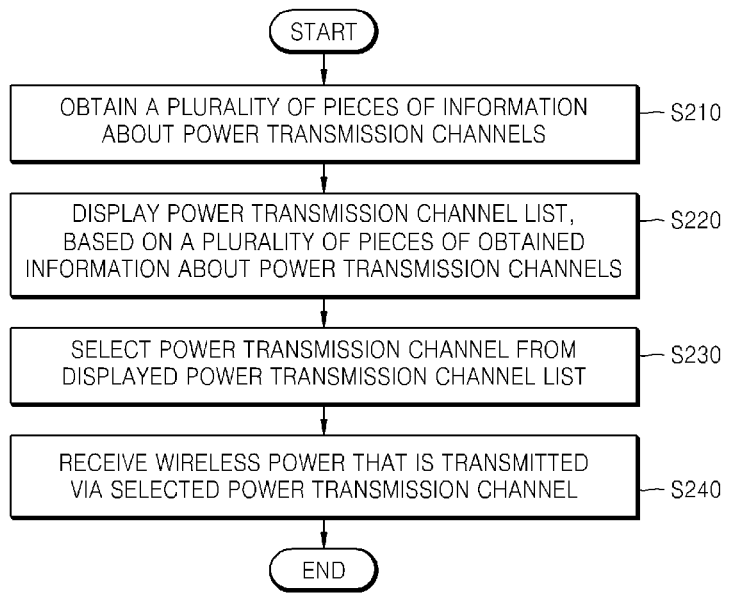
FIG. 2 is a flowchart of an operating method of an ultrasound probe, according to an embodiment of the present invention.

FIG. 2 is a flowchart of an operating method of the ultrasound probe 400, according to an embodiment of the present invention.

In operation S210, the ultrasound probe 400 may obtain information about each of power transmission channels.

Here, the "power transmission channel" may correspond to a device capable of wirelessly supplying power to the ultrasound probe 400. For example, the power transmission channel may be included in an ultrasound diagnosis apparatus that communicates with the ultrasound probe 400, or may be a device that is separate from the ultrasound diagnosis apparatus. The plurality of power transmission channels may use different wireless power transmission modes, respectively, or may use the same wireless power transmission mode.

The "information about each power transmission channel" may include a name of the power transmission channel, a wireless power transmission mode used by the power transmission channel, a position of the power transmission channel, or a characteristic value of wireless power that is transmitted by the power transmission channel. The "wireless power transmission mode" may include at least one of an electromagnetic induction method, an electromagnetic radiation method, an electromagnetic resonance method, and a wireless power transmission mode using an ultrasound. The "characteristic value of the wireless power" may include a value of at least one of a voltage of the wireless power, a current of the wireless power, and a frequency of the wireless power.

In an embodiment, the ultrasound probe 400 may sense a characteristic value of wireless power that is transmitted by each of the power transmission channels, and then may obtain the sensed characteristic value as information about each power transmission channel. In another embodiment, the ultrasound probe 400 may receive a data signal including information about the power transmission channel, wherein the data signal is transmitted by each of the power transmission channels, so that the ultrasound probe 400 may obtain information about each of the power transmission channels based on the data signal. The data signal that the ultrasound probe 400 receives from each of the power transmission channels may include information about a value of at least one of a voltage of the wireless power, a current of the wireless power, and a frequency of the wireless power.

In operation S220, the ultrasound probe 400 may display a power transmission channel list, based on the information about each of the plurality of power transmission channels obtained in operation S210.

The power transmission channel list may display identifiers (e.g., names, allocated numbers, allocated letters, or allocated symbols of the power transmission channels) that correspond to the power transmission channels, and the information about each of the power transmission channels obtained in operation S210. For example, the power transmission channel list may include information about wireless power transmission modes that are used by the power transmission channels to transmit wireless power to the ultrasound probe 400.

The ultrasound probe 400 may list at least some of a plurality of pieces of information about the power transmission channels, on the power transmission channel list, based on a priority order of the power transmission channels. The priority order of the power transmission channels may be previously stored in the ultrasound probe 400 or may be determined based on user input information. Alternatively, the priority order of the power transmission channels may be automatically determined according to the plurality of pieces of information about the power transmission channels which are obtained in operation S210.

For example, the ultrasound probe 400 may store priority orders of the power transmission channels that are expected to transmit wireless power, based on a level of stable transmission of the wireless power, e.g., based on a strength of the wireless power to be transmitted.

In a storage unit 470 (refer to FIG. 5) of the ultrasound probe 400, the identifiers of the power transmission channels may be stored while the identifiers match with the priority orders. Thus, the ultrasound probe 400 may obtain the identifiers of the power transmission channels now capable of transmitting wireless power to the ultrasound probe 400, by referring to the plurality of pieces of information about the power transmission channels, and may check the priority orders of the power transmission channels stored in the storage unit 470.

The ultrasound probe 400 may list at least some of the identifiers of the power transmission channels and the plurality of pieces of information about the power transmission channels on the power transmission channel list, based on the checked priority orders.

In another embodiment, the ultrasound probe 400 may determine priority orders of the power transmission channels, based on the plurality of pieces of information about the power transmission channels. The ultrasound probe 400 may determine the priority orders of the power transmission channels, based on a voltage, a current, a power, and a frequency of wireless power that is received from each of the power transmission channels, and/or based on the wireless power transmission modes that are used by the power transmission channels.

For example, the ultrasound probe 400 may allocate a highest priority order to a power transmission channel that transmits a strongest wireless power or may allocate a highest priority order to a power transmission channel that transmits wireless power having a frequency that is the most similar to a frequency of wireless power that the ultrasound probe 400 can receive. In operation S230, the ultrasound probe 400 may select a power transmission channel from the power transmission channel list that is displayed in operation S220. When the power transmission channels are available, the ultrasound probe 400 may automatically or manually select at least one power transmission channel so as to achieve the most excellent connection state.

For example, the ultrasound probe 400 may select a power transmission channel, based on a predetermined input. The input that involves selecting the power transmission channel may be a command that is input by the user or is previously stored in the storage unit 470.

The ultrasound probe 400 may recognize a user input related to selection of at least one power transmission channel from the displayed power transmission channel list. The ultrasound probe 400 may select the user-selected power transmission channel, based on the recognized user input.

For example, the user may input a command related to selection of the power transmission channel, via a user input unit 430 (refer to FIG. 5) included in the ultrasound probe 400. Alternatively, the user may input the command related to selection of the power transmission channel, via an external device that communicates with the ultrasound probe 400. For example the external device that communicates with the ultrasound probe 400 may include an ultrasound diagnosis apparatus that provides an ultrasound image to the user by receiving ultrasound image data that is generated by the ultrasound probe 400.

In operation S240, the ultrasound probe 400 may receive wireless power that is transmitted via the power transmission channel selected in operation S230.

The ultrasound probe 400 may convert the received wireless power so as to make the received wireless power appropriate for use by the ultrasound probe 400. That is, the ultrasound probe 400 may use the received wireless power after the ultrasound probe 400 converts the received wireless power to be below a rated voltage and a rated current of the ultrasound probe 400.

For example, the ultrasound probe 400 may convert the received wireless power by using a switched-mode power supply (SMPS) included in the ultrasound probe 400.

In the ultrasound system 100 shown in FIG. 1, the ultrasound diagnosis apparatus 120 may be wirelessly connected with the wireless ultrasound probe 110, so that the ultrasound diagnosis apparatus 120 may generate the ultrasound image by using the ultrasound image data transmitted by the wireless ultrasound probe 110, and may display the ultrasound image. When the ultrasound diagnosis apparatus 120 provides the ultrasound image data for a diagnosis to a user in real-time, it is required for the wireless ultrasound probe 110 to seamlessly provide the ultrasound image data to the ultrasound diagnosis apparatus 120.

Thus, in order for the wireless ultrasound probe 110 to seamlessly provide the ultrasound image data to the ultrasound diagnosis apparatus 120, the wireless ultrasound probe 110 has to stably receive wireless power.

When reception of wireless power via the power transmission channel is discontinued, the ultrasound probe 400 capable of stably receiving wireless power may provide information indicating that the reception of the wireless power is discontinued.

Thus, according to the information from the ultrasound probe 400, the user may input a command to the ultrasound probe 400, wherein the command involves searching for and selecting another power transmission channel capable of supplying wireless power. Alternatively, the user may input a command to the ultrasound probe 400, wherein the command involves using a power of a battery 456 (refer to FIG. 5) that is embedded in the ultrasound probe 400.

Also, in another embodiment, when reception of wireless power via the power transmission channel is discontinued, the ultrasound probe 400 may receive wireless power that is transmitted via another power transmission channel. A detailed operating method of the ultrasound probe 400 capable of stably receiving wireless power is now described with reference to FIG. 3.

Figure 3:
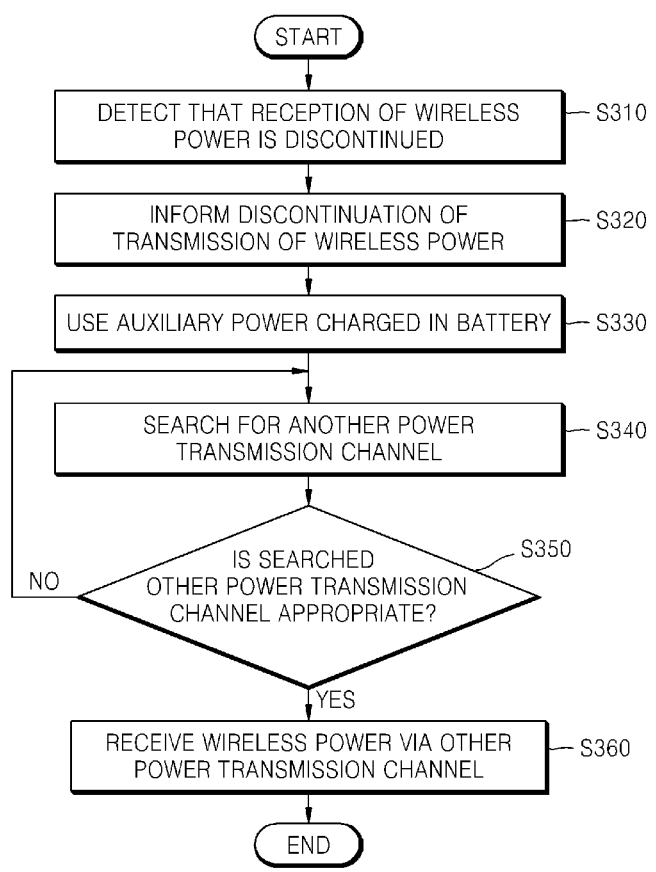
FIG. 3 is a flowchart of an operating method of the ultrasound probe when reception of a wireless power is discontinued, according to an embodiment of the present invention.

FIG. 3 is a flowchart of an operating method of the ultrasound probe 400 when reception of wireless power is discontinued, according to an embodiment of the present invention.

In operation S310, the ultrasound probe 400 may detect that reception of wireless power being transmitted via the power transmission channel selected in operation S230 of FIG. 2 has been discontinued. The ultrasound probe 400 may periodically determine whether the wireless power is being received as normal. The ultrasound probe 400 may determine the normal reception of the wireless power by using at least one of a voltage, a current, a power, and a frequency of the received wireless power. Alternatively, the ultrasound probe 400 may detect that the reception of the wireless power has been discontinued based on a data signal it receives indicating discontinuation of the transmission of the wireless power.

In operation S320, the ultrasound probe 400 may inform a user of the discontinuation of the transmission of the wireless power which is detected in operation S310. Information indicating the discontinuation of the transmission of the wireless power may be provided in the form of a moving picture, a still image, a symbol, text, or sound.

In operation S330, the ultrasound probe 400 may operate by using power charged in the battery 456 that is embedded in the ultrasound probe 400. That is, the ultrasound probe 400 may replace the wireless power, which is transmitted by the external power transmission channel, with the power charged in the battery 456, as power to operate the ultrasound probe 400.

In operation S340, the ultrasound probe 400 may search for another power transmission channel from among the power transmission channels. In order to search for another power transmission channel, the ultrasound probe 400 may again perform the operation of obtaining the plurality of pieces of information about the power transmission channels which is shown in operation S210 of FIG. 2. The ultrasound probe 400 may search for the other power transmission channel, based on the plurality of pieces of information about the power transmission channels which are obtained again.

Alternatively, the ultrasound probe 400 may search for another power transmission channel as an alternative power transmission channel, from power transmission channels that are rated based on their respective priority orders. The other power transmission channel that was previously ranked second in the priority orders of the power transmission channels is selected. Here, the priority orders of the power transmission channels may be automatically determined according to the plurality of pieces of information about the power transmission channels or may be manually determined based on a user input.

In operation S350, the ultrasound probe 400 may determine whether the other power transmission channel, which is searched in operation S340, is appropriate to transmit wireless power to the ultrasound probe 400. Whether the other power transmission channel is appropriate to transmit the wireless power to the ultrasound probe 400 may be determined based on at least one of a voltage, a current, a power, and a frequency of the wireless power that is transmitted by the other power transmission channel.

For example, when the voltage and the current of the wireless power that is transmitted by the other power transmission channel are equal to or less than a rated current and a rated voltage for the ultrasound probe 400, and are sufficient enough to operate the ultrasound probe 400, the ultrasound probe 400 may determine that the other power transmission channel is appropriate to transmit the wireless power to the ultrasound probe 400.

When the other power transmission channel is not appropriate to transmit the wireless power to the ultrasound probe 400, the ultrasound probe 400 may return to operation S340 and then may search for another power transmission channel.

When the other power transmission channel is appropriate to transmit the wireless power to the ultrasound probe 400, in operation S360, the ultrasound probe 400 may receive wireless power via the other power transmission channel selected.

Figure 4:
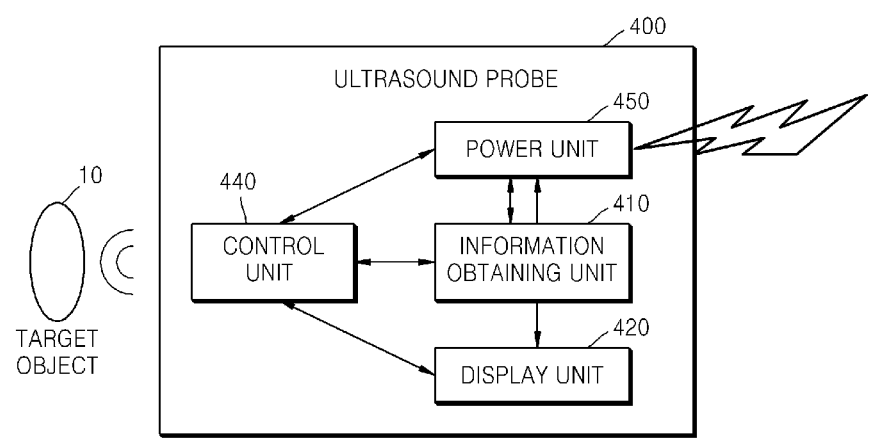
FIG. 4 is a block diagram of the ultrasound probe, according to an embodiment of the present invention.

FIG. 4 is a block diagram of the ultrasound probe 400, according to an embodiment of the present invention.

The ultrasound probe 400 may transmit an ultrasound signal to a target object, may receive an ultrasound signal (e.g., an ultrasound echo signal) that is reflected from the target object, and then may generate a reception signal. The ultrasound probe 400 may focus the reception signal, thereby generating ultrasound image data used in generation of an ultrasound image.

The ultrasound probe 400 may generate the ultrasound image data and then may transmit the generated ultrasound image data to an external device. Here, the "external device" that receives the generated ultrasound image data may include an ultrasound diagnosis apparatus, a display device, a personal computer (PC), a server, or the like.

In another embodiment, the ultrasound probe 400 may include a predetermined ultrasound diagnosis apparatus (not shown). In this case, the ultrasound probe 400 may generate and display the ultrasound image after processing the ultrasound image data that is generated by the ultrasound probe 400.

Elements of the ultrasound probe 400 are configured to perform operations that constitute the operating method of ultrasound probe 400 in FIG. 2. Thus, hereinafter, although descriptions are omitted, if the descriptions are provided above with reference to the operating method of ultrasound probe 400 in FIG. 2, the descriptions may also be applied to the ultrasound probe 400 shown in FIG. 4.

The ultrasound probe 400 may include an information obtaining unit 410, a display unit 420, a control unit 440, and a power unit 450.

The information obtaining unit 410 may obtain a plurality of pieces of information about power transmission channels capable of transmitting wireless power to the ultrasound probe 400. The information obtaining unit 410 may receive a data signal or may detect wireless power so as to obtain the plurality of pieces of information about power transmission channels.

The display unit 420 may display a power transmission channel list, based on the plurality of pieces of information about power transmission channels which are obtained by the information obtaining unit 410. The power transmission channel list may include the plurality of pieces of information about power transmission channels.

For example, the display unit 420 may display identifiers (e.g., names, allocated numbers, allocated letters, or allocated symbols of the power transmission channels) that correspond to the power transmission channels. Also, the display unit 420 may display at least one of a wireless power transmission mode, a position, a characteristic value (e.g., a voltage, a current, and a frequency) of wireless power, which are related to at least one power transmission channel from among the power transmission channels.

Also, the display unit 420 may display state information related to an operation required to obtain ultrasound image data, a user interface (UI) or a GUI which is related to function setting, and an ultrasound image of the target object.

When a display panel of the display unit 420 and a touch pad to be described later form a mutual layer structure and thus are formed as a touch screen, the display unit 420 may be used as both an output device and an input device.

The display unit 420 may include at least one of a liquid crystal display (LCD), a thin film transistor-liquid crystal display (TFT-LCD), an organic light-emitting display device, a flexible display, a three-dimensional (3D) display, and an electrophoretic display.

The control unit 440 may control all operations of the ultrasound probe 400 and may select a power transmission channel from power transmission channel list that is displayed by the display unit 420. Also, the control unit 440 may control the information obtaining unit 410, the display unit 420, and the power unit 450 so as to receive wireless power from the selected power transmission channel.

The power unit 450 may receive the wireless power that is transmitted via the power transmission channel selected by the control unit 440. Also, the power unit 450 may supply the received wireless power to the information obtaining unit 410, the display unit 420, and the control unit 440.

Figure 5:
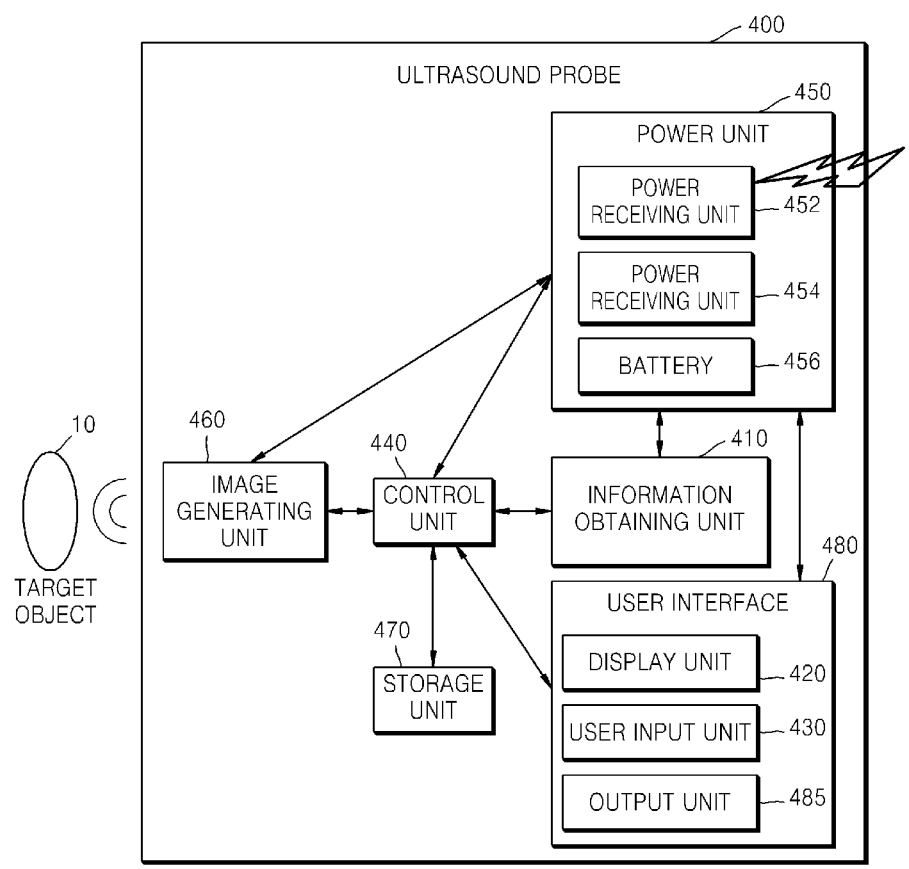
FIG. 5 is a block diagram of the ultrasound probe, according to another embodiment of the present invention.

FIG. 5 is a block diagram of the ultrasound probe 400, according to another embodiment of the present invention.

In the present embodiment, the ultrasound probe 400 may further include an image generating unit 460, the storage unit 470, and a user interface 480. Also, the power unit 450 may include a power receiving unit 452, a power converting unit 454, and the battery 456.

The information obtaining unit 410, the display unit 420, the user input unit 430, the control unit 440, and the power unit 450 of the ultrasound probe 400 which are shown in FIG. 5 correspond to those of FIG. 4, and thus, corresponding descriptions are omitted here.

The image generating unit 460 may transmit an ultrasound signal to a target object and may generate a reception signal by receiving an ultrasound signal (e.g., an ultrasound echo signal) that is reflected from the target object.

The storage unit 470 stores various types of information required by the ultrasound probe 400 to operate. For example, the storage unit 470 may store, but is not limited to, the ultrasound signal that is transmitted by the image generating unit 460, the ultrasound echo signal that is input to the image generating unit 460, or information about a plurality of pieces of information about the power transmission channels which are obtained by the information obtaining unit 410.

The user interface 480 provides information related to operations of the ultrasound probe 400 to a user, and receives various types of an input for controlling the ultrasound probe 400 from the user. The user interface 480 may provide the information to the user by displaying a GUI related to function setting for the ultrasound probe 400 or by reproducing audio data, and may display an ultrasound image that is formed based on the reception signal formed by the image generating unit 460.

The user interface 480 may include the display unit 420 and the user input unit 430, and may further include an output unit 485. The output unit 485 is different from the display unit 420 and functions to inform the user of a mechanical error such as discontinuation of reception of wireless power, and for example, the output unit 485 may include a light-emitting diode (LED), or the like.

The user input unit 430 may receive an input that selects a power transmission channel from the power transmission channel list displayed on the display unit 420. Thus, the control unit 440 may select the power transmission channel based on the input received by the user input unit 430.

The user input unit 430 may be formed of, but is not limited to, a key pad, a mouse, a dome switch, a touch pad (a touch capacitive type touch pad, a pressure resistive type touch pad, an infrared beam sensing type touch pad, a surface acoustic wave type touch pad, an integral strain gauge type touch pad, a Piezo effect type touch pad, or the like), a jog wheel, a jog switch, or the like. Also, the user input unit 430 may further include a communication unit (not shown) that receives a user input via an external device that communicates with the ultrasound probe 400.

The power receiving unit 452 may receive wireless power from the power transmission channels.

The power converting unit 454 may convert the received wireless power so as to make the received wireless power appropriate to be supplied to each of elements included in the ultrasound probe 400. That is, the power converting unit 454 may convert the received wireless power so that the received wireless power is below a rated voltage and a rated current of the ultrasound probe 400. For example, the power converting unit 454 may convert the received wireless power by using an SMPS, a voltage boosting device, and/or a voltage dropping device.

The battery 456 may be charged due to the wireless power received from the power transmission channels. The battery 456 may supply the charged power to each of the elements included in the ultrasound probe 400, in response to a control signal from the control unit 440.

Also, the battery 456 may be controlled by the control unit 440 so as to supply only a predetermined percentage of the charged power to the image generating unit 460. The control unit 440 may determine the predetermined percentage of the charged power to be supplied to the image generating unit 460, according to a user input.

The battery 456 may include a main battery (not shown) and an auxiliary battery (not shown), wherein the main battery supplies power that is required by the ultrasound probe 400 to generate ultrasound image data and to transmit the ultrasound image data to an outer source, and the auxiliary battery supplies power that is required by the ultrasound probe 400 when the ultrasound probe 400 is in a standby mode or performs a boot-up operation.

Figure 6A:
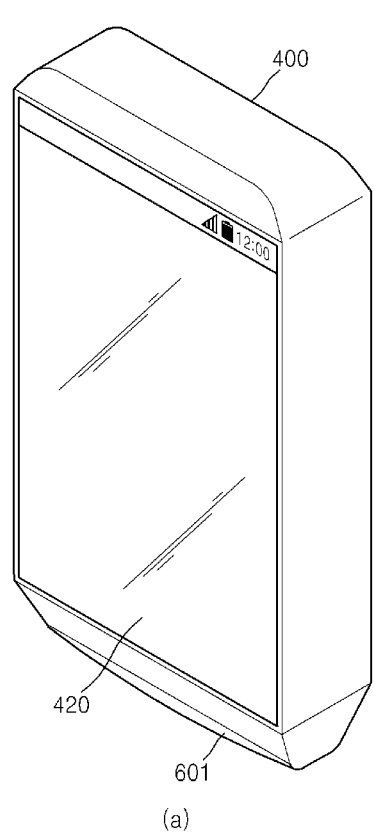
FIGS. 6A and 6B are diagrams illustrating the ultrasound probe, according to an embodiment of the present invention.
Figure 6B:
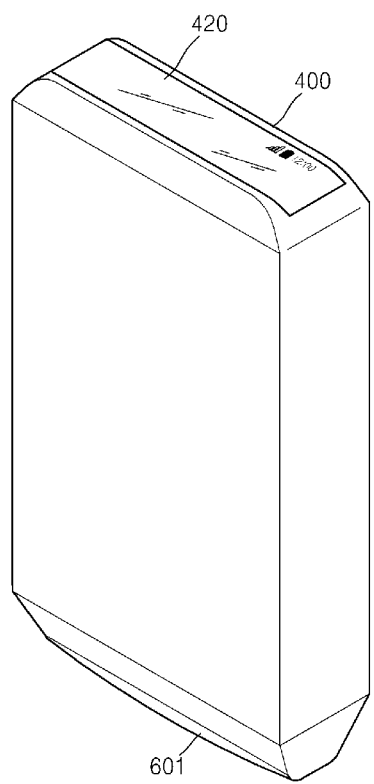

FIGS. 6A and 6B are diagrams illustrating the ultrasound probe 400, according to an embodiment of the present invention.

As illustrated in FIG. 6A, the display unit 420 may be disposed at a side surface of the ultrasound probe 400 with respect to a bottom surface 601 of the ultrasound probe 400, wherein a transducer for receiving an ultrasound signal about a target object is disposed at the bottom surface 601.

Also, as illustrated in FIG. 6B, the display unit 420 may be disposed at a top surface of the ultrasound probe 400. When the display unit 420 is disposed at the top surface, although a user scans a target object while the user holds the side surface of the ultrasound probe 400, a user's hand does not obstruct the display unit 420 so that readability of information that is provided by the ultrasound probe 400 is increased.

The display unit 420 may display a reception state of wireless power or reception of data communication, in the form of text or an image. Also, the display unit 420 may display a power state of the battery 456. For example, the display unit 420 may display whether the battery 456 is being charged, whether the battery 456 needs to be charged, a remaining power level of the battery, or the like, in the form of text or an image.

Figure 7:
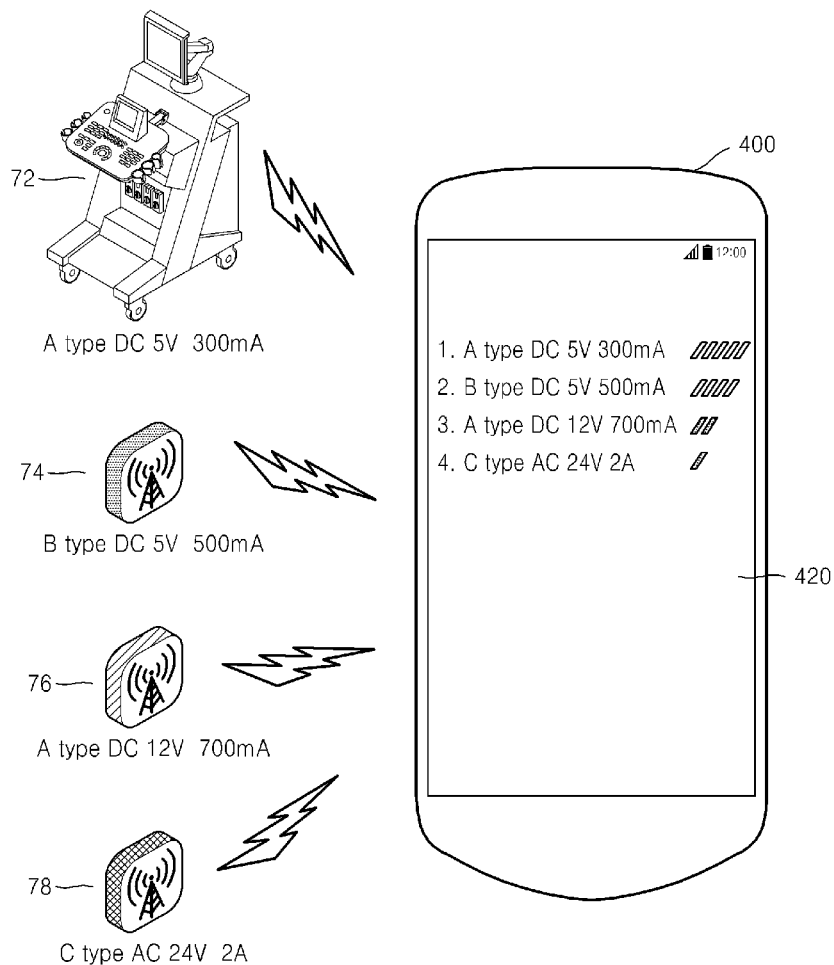
FIG. 7 illustrates a screen that is displayed on the ultrasound probe, according to an embodiment of the present invention.

FIG. 7 illustrates a screen that is displayed on the ultrasound probe 400, according to an embodiment of the present invention.

Referring to FIG. 7, the ultrasound probe 400, and power transmission channels 72, 74, 76, and 78 capable of transmitting wireless power to the ultrasound probe 400 are illustrated.

As illustrated in FIG. 7, the ultrasound probe 400 may display a power transmission channel list on the display unit 420, according to a plurality of pieces of information about the power transmission channels 72, 74, 76, and 78.

The power transmission channel list that is displayed on the ultrasound probe 400 includes wireless power transmission modes by which the power transmission channels 72, 74, 76, and 78 transmit wireless power to the ultrasound probe 400; whether the transmitted wireless power is alternating current (AC) power or direct current (DC) power; a voltage and current of the transmitted wireless power; and whether the transmitted wireless power is appropriate to the ultrasound probe 400.

For example, it is assumed that the power transmission channel 72 is an ultrasound diagnosis apparatus, uses an A method as the wireless power transmission mode so as to transmit power, transmits DC power, and transmits wireless power of about 5V 300 mA. The ultrasound probe 400 obtains the information about the power transmission channel 72 and then displays [A type DC 5V 300 mA] as illustrated in FIG. 7.

For example, the ultrasound probe 400 shown in FIG. 7 allows a rated voltage of 10V and a rated current of 1A. Thus, the power transmission channel 72 and the power transmission channel 74 satisfy the rated voltage and the rated current of the ultrasound probe 400, so that the ultrasound probe 400 may determine that wireless power transmitted by the power transmission channel 72 and the power transmission channel 74 is appropriate to the ultrasound probe 400. Information indicating that the wireless power transmitted by the power transmission channel 72 and the power transmission channel 74 is appropriate to the ultrasound probe 400 may be provided via the display unit 420. Whether the wireless power is appropriate to the ultrasound probe 400 may be expressed in the form of a figure, text, or a color.

Since the power transmission channel 76 and the power transmission channel 78 do not satisfy the rated voltage and the rated current of the ultrasound probe 400, the ultrasound probe 400 may determine that wireless power transmitted by the power transmission channel 76 and the power transmission channel 78 is not appropriate to the ultrasound probe 400. Information indicating that the wireless power transmitted by the power transmission channel 76 and the power transmission channel 78 is not appropriate to the ultrasound probe 400 may be provided via the display unit 420.

For example, the ultrasound probe 400 may express strength of wireless power transmitted by each of the power transmission channels 72, 74, 76, and 78, by using a number of bars. Alternatively, the ultrasound probe 400 may express whether a certain power transmission channel is appropriate to transmit wireless power to the ultrasound probe 400, by using a number of bars. Referring to FIG. 7, the power transmission channel 72 having a largest number of bars is determined as the most appropriate channel.

Figure 8:
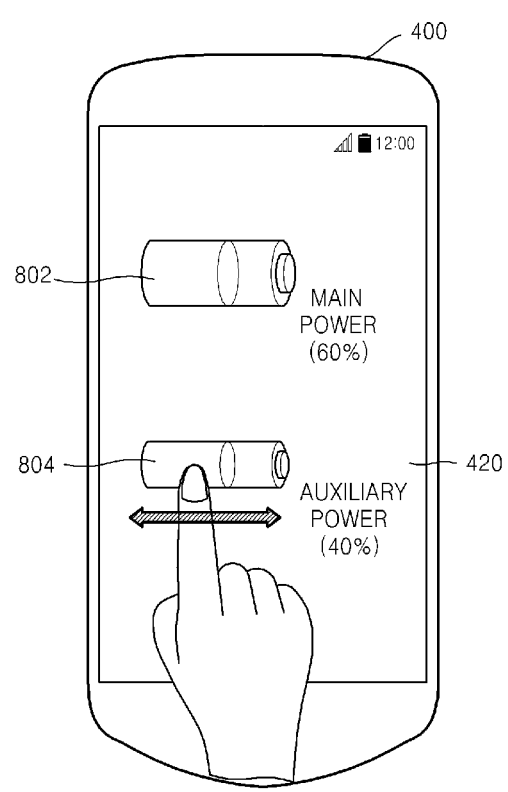
FIG. 8 illustrates a screen that is displayed on the ultrasound probe and that allows a user to adjust a usage percentage of power charged in a battery, according to an embodiment of the present invention.

FIG. 8 illustrates a screen that is displayed on the ultrasound probe 400 and that allows a user to adjust a usage percentage of a power charged in a battery, according to an embodiment of the present invention.

The ultrasound probe 400 may include at least one battery that performs both a function of a main battery and a function of an auxiliary battery.

The main battery may be a battery that supplies power that is required by the ultrasound probe 400 to generate ultrasound image data and to transmit the ultrasound image data to an outer source, and the auxiliary battery may be a battery that supplies power that is required by the ultrasound probe 400 when the ultrasound probe 400 is in a standby mode or performs a boot-up operation. For example, the ultrasound probe 400 may use only a portion of the power charged in the battery so as to generate the ultrasound image data.

In order to make one battery perform both the function of the main battery and the function of the auxiliary battery, it is required to determine a percentage of main power and a percentage of auxiliary power from among the power that is charged in the battery.

As illustrated in FIG. 8, the ultrasound probe 400 may provide a UI for receiving a user input that involves determining the ratio of the main power and the auxiliary power.

FIG. 8 illustrates an image 802 and an image 804, wherein the image 802 displays a percentage of power that is allocated as the main power of the power charged in the battery, and the image 804 displays a percentage of power that is allocated as the auxiliary power of the power charged in the battery. For example, as illustrated in FIG. 8, a user may touch or drag the image 802 and the image 804, thereby inputting the percentage of the main power and the percentage of the auxiliary power.

When the ultrasound probe 400 measures the remaining power in the battery, the ultrasound probe 400 may measure the remaining power, based on the amounts of power that are allocated as the main power and the auxiliary power, respectively.

It is assumed that, as illustrated in FIG. 8, the ultrasound probe 400 operates while the ultrasound probe 400 uses 60% of the power charged in the battery as the main power source, and 40% of the power as the auxiliary power source.

The ultrasound probe 400 uses only the power that is allocated as the main power source for generating ultrasound image data and transmitting the ultrasound image data to an outer source. Thus, although the main power source is totally consumed, the battery may still have the power that is allocated as the auxiliary power source. However, when the ultrasound probe 400 measures the remaining power in the battery, the ultrasound probe 400 measures the remaining power based on the power that is allocated as the main power source.

Thus, although the battery actually has the remaining power, since the percentage of the power which is allocated as the main power source is totally consumed, the ultrasound probe 400 may provide the user of information indicating necessity of battery charging due to a low remaining power of the battery.

Figure 9:
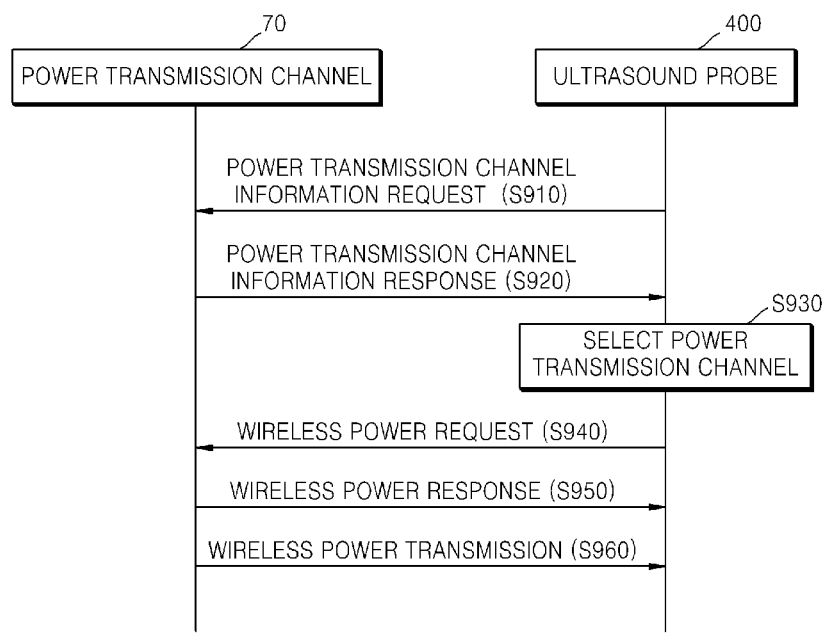
FIG. 9 is a signal flowchart of a procedure in which the ultrasound probe selects a power transmission channel and receives wireless power, according to an embodiment of the present invention.

FIG. 9 is a signal flowchart of a procedure in which the ultrasound probe 400 selects a power transmission channel 70 and receives wireless power, according to an embodiment of the present invention. In order for the ultrasound probe 400 to select the power transmission channel 70 and to receive the wireless power, a general data communication method and a general wireless power transmission and reception method may be all used.

In operation S910, the ultrasound probe 400 may request information about the power transmission channel 70. The requested information about the power transmission channel 70 may include at least one of an identifier of the power transmission channel 70, an address of the power transmission channel 70, and a characteristic value of wireless power that is transmitted by the power transmission channel 70.

In operation S920, the power transmission channel 70 may transmit the information about the power transmission channel 70, in response to the request from the ultrasound probe 400.

In operation S930, the ultrasound probe 400 may select the power transmission channel 70 as the source from which it will receive wireless power, based on the received information about the power transmission channel 70.

In operation S940, the ultrasound probe 400 may request the power transmission channel 70 to transmit the wireless power. Here, wireless power request data from the ultrasound probe 400 may include information about a protocol or synchronization for transmission and reception of the wireless power.

In operation S950, the ultrasound probe 400 may receive a response with respect to the wireless power request data, from the power transmission channel 70. Here, a wireless power response from the power transmission channel 70 may include information about the protocol or synchronization for transmission and reception of the wireless power.

In operation S960, the ultrasound probe 400 may receive the wireless power that is transmitted by the power transmission channel 70 selected in operation S930.

Figure 10:
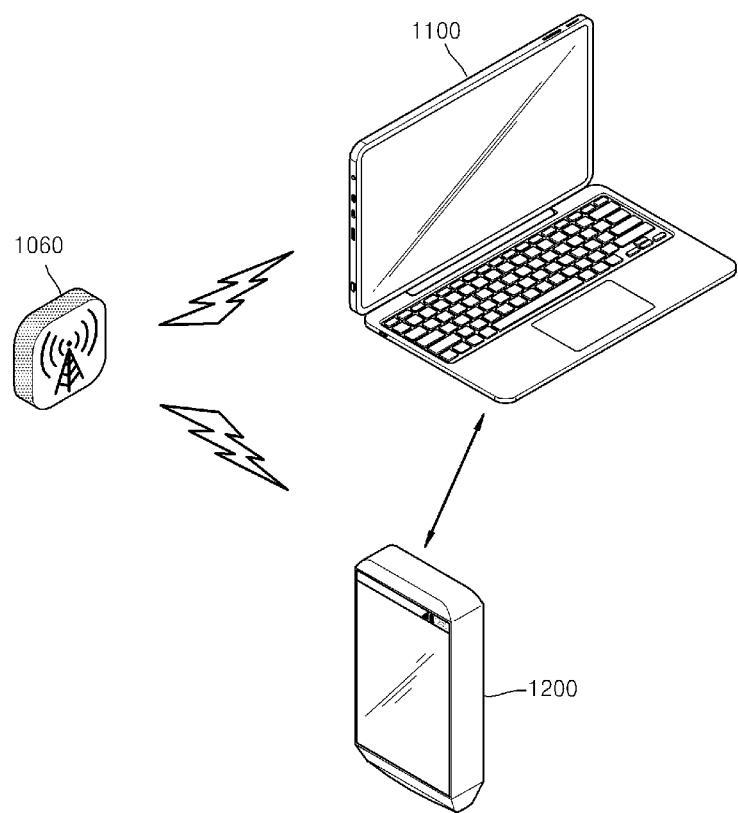
FIG. 10 illustrates an ultrasound system including an ultrasound probe and an ultrasound diagnosis apparatus according to another embodiment of the present invention.

FIG. 10 illustrates an ultrasound system including an ultrasound probe 1200 and an ultrasound diagnosis apparatus 1100 according to another embodiment of the present invention.

Referring to FIG. 10, the ultrasound system may include the ultrasound diagnosis apparatus 1100 and the ultrasound probe 1200 that are wirelessly connected.

The ultrasound diagnosis apparatus 1100 may be HCU equipment that a user may carry but is not limited thereto.

The ultrasound probe 1200 may communicate with not only the ultrasound diagnosis apparatus 1100 but also communicate with other ultrasound diagnosis apparatuses. However, the ultrasound probe 1200 may be temporarily subordinate to the ultrasound diagnosis apparatus 1100 that is wirelessly connected with the ultrasound probe 1200.

The fact that the ultrasound probe 1200 is subordinate to the ultrasound diagnosis apparatus 1100 may mean that a pairing is linked between the ultrasound probe 1200 and the ultrasound diagnosis apparatus 1100 so that a session is established.

The term "session" may mean logical connection for communication between the ultrasound diagnosis apparatus 1100 and the ultrasound probe 1200. In order to form the session, it is required to perform a process in which the ultrasound diagnosis apparatus 1100 and the ultrasound probe 1200 exchange an message and thus recognize each other.

The ultrasound diagnosis apparatus 1100 may transmit a control signal to the ultrasound probe 1200 via the session. The ultrasound probe 1200 may be controlled by the control signal transmitted by the ultrasound diagnosis apparatus 1100. Also, the ultrasound probe 1200 may transmit ultrasound image data formed by the ultrasound probe 1200 to the ultrasound diagnosis apparatus 1100 via the session.

The ultrasound diagnosis apparatus 1100 may select a wireless power transmission channel 1060 in an environment in which a plurality of wireless power transmission channels (hereinafter, referred as 'power transmission channels') exist, and may transmit information about the selected power transmission channel 1060 to the ultrasound probe 1200 via the session.

Here, the "power transmission channel 1060" may indicate a device capable of wirelessly supplying a power to an apparatus. The power transmission channel 1060 may include the ultrasound diagnosis apparatus 1100 connected with the ultrasound probe 1200, or may be an independent device separate from the ultrasound probe 1200.

The power transmission channels may use different wireless power transmission modes or the same wireless power transmission mode.

Here, the "wireless power transmission mode" may include an electromagnetic induction method based on electromagnetic induction that is generated due to a wireless power signal, an electromagnetic resonance method based on electromagnetic resonance that is generated due to a wireless power signal having a particular frequency, an electromagnetic radiation method (i.e., a non-radiation type wireless energy transmission method) based on electromagnetic radiation, a wireless power transmission mode (refer to U.S. Pat. No. 6,798,716 by Arthur Charych, which is about energy transmission using ultrasound), and any method that is similar to one of the aforementioned methods.

For example, the ultrasound diagnosis apparatus 1100 may transmit, to the ultrasound probe 1200, the information about the selected power transmission channel 1060 from which the ultrasound diagnosis apparatus 1100 receives a wireless power, and thus may allow the ultrasound probe 1200 to receive the wireless power from the power transmission channel 1060.

Also, the ultrasound diagnosis apparatus 1100 may transmit a control signal controlling the ultrasound probe 1200 to receive the wireless power from the power transmission channel 1060 and to be charged.

Thus, the ultrasound probe 1200 may automatically receive the wireless power in response to the control signal from the ultrasound diagnosis apparatus 1100 and may be charged with the wireless power without a separate user input of charging the ultrasound probe 1200.

Hereinafter, with reference to FIGS. 11 through 13, a method of transmitting information about a power transmission channel to the ultrasound probe 1200, the method performed by the ultrasound diagnosis apparatus 1100, will be described in detail. Also, with reference to FIG. 14, a method of receiving information about a power transmission channel and then receiving a wireless power from the ultrasound diagnosis apparatus 1100, the method performed by the ultrasound probe 1200, will be described in detail.

Figure 11:
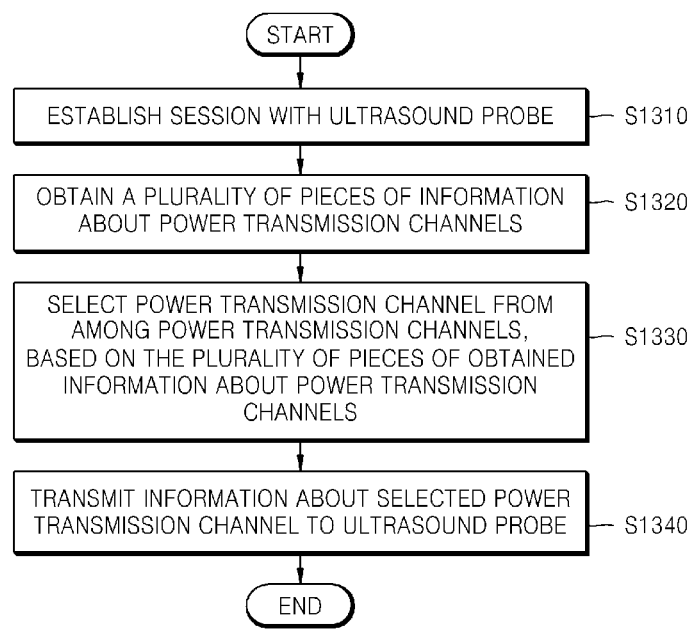
FIG. 11 is a flowchart of an operating method of an ultrasound diagnosis apparatus, according to an embodiment of the present invention.

FIG. 11 is a flowchart of an operating method of the ultrasound diagnosis apparatus 1100, according to an embodiment of the present invention.

In operation S1310, the ultrasound diagnosis apparatus 1100 may establish a session with the ultrasound probe 1200.

When the session is established between the ultrasound diagnosis apparatus 1100 and the ultrasound probe 1200, the ultrasound probe 1200 may be temporarily subordinate to the ultrasound diagnosis apparatus 1100.

In operation S1320, the ultrasound diagnosis apparatus 1100 may obtain a plurality of pieces of information about power transmission channels.

Here, information about a power transmission channel may include information that is used by the ultrasound probe 1200 so as to receive a wireless power from the power transmission channel. For example, the information about the power transmission channel may include information about at least one of an identifier (e.g., a name, an identification code, etc. of the power transmission channel) of the power transmission channel, a method by which the power transmission channel transmits the wireless power, a location of the power transmission channel, and a characteristic value of the wireless power transmitted by the power transmission channel.

The characteristic value of the wireless power may include at least one of a voltage of the wireless power, current of the wireless power, and a frequency of the wireless power.

For one example, the ultrasound diagnosis apparatus 1100 may sense characteristic values of wireless powers received from the power transmission channels, and thus may obtain the sensed characteristic values as the plurality of pieces of information about the power transmission channels.

For another example, the ultrasound diagnosis apparatus 1100 may obtain the information about each of the power transmission channels by receiving a data signal that is received from each of the power transmission channels and includes the information about each of the power transmission channels. The data signal that includes the information about each of the power transmission channels may be wiredly or wirelessly received via a network.

In operation S1330, the ultrasound diagnosis apparatus 1100 may select at least one power transmission channel from among the power transmission channels, based on the plurality of pieces of information about the power transmission channels that are obtained in operation S1320. The selected power transmission channel may be a target power transmission channel from which the ultrasound probe 1200 is to receive a wireless power.

The ultrasound diagnosis apparatus 1100 may select the power transmission channel from among the power transmission channels, in an automatic manner or based on a user input.

The ultrasound diagnosis apparatus 1100 may provide a GUI to a user so as to receive an input of selecting the power transmission channel from the user.

The ultrasound diagnosis apparatus 1100 may select a power transmission channel that is the most appropriate for the ultrasound probe 1200 to receive the wireless power, based on information about the ultrasound probe 1200 and the information about each of the power transmission channels. In this case, in order to select the power transmission channel, the ultrasound diagnosis apparatus 1100 may further obtain the information about the ultrasound probe 1200.

The operation of selecting the power transmission channel, the operation performed by the ultrasound diagnosis apparatus 1100, will be described in detail with reference to FIG. 12.

In operation S1340, the ultrasound diagnosis apparatus 1100 may transmit information about the power transmission channel selected in operation S1330, to the ultrasound probe 1200 via the session.

The information about the selected power transmission channel which is transmitted by the ultrasound diagnosis apparatus 1100 may correspond to information that is used by the ultrasound probe 1200 so as to receive the wireless power from the selected power transmission channel.

The information transmitted by the ultrasound diagnosis apparatus 1100 to the ultrasound probe 1200 may include at least one of an identifier of the selected power transmission channel, a characteristic value of the wireless power transmitted by the selected power transmission channel, and a wireless power transmission mode used by the selected power transmission channel so as to transmit the wireless power.

When the ultrasound diagnosis apparatus 1100 is booted up, the ultrasound diagnosis apparatus 1100 may transmit information about a power transmission channel to the ultrasound probe 1200. Alternatively, when the ultrasound diagnosis apparatus 1100 receives a wireless power from the power transmission channel, the ultrasound diagnosis apparatus 1100 may transmit the information about the power transmission channel to the ultrasound probe 1200.

Also, the ultrasound diagnosis apparatus 1100 may obtain, from the ultrasound probe 1200, information about a remaining power of a battery in the ultrasound probe 1200. When the remaining power of the battery is equal to or less than a predetermined value, the ultrasound diagnosis apparatus 1100 may transmit, to the ultrasound probe 1200, a control signal for controlling the ultrasound probe 1200 to receive the wireless power from the power transmission channel selected in operation S1330.

Figure 12:
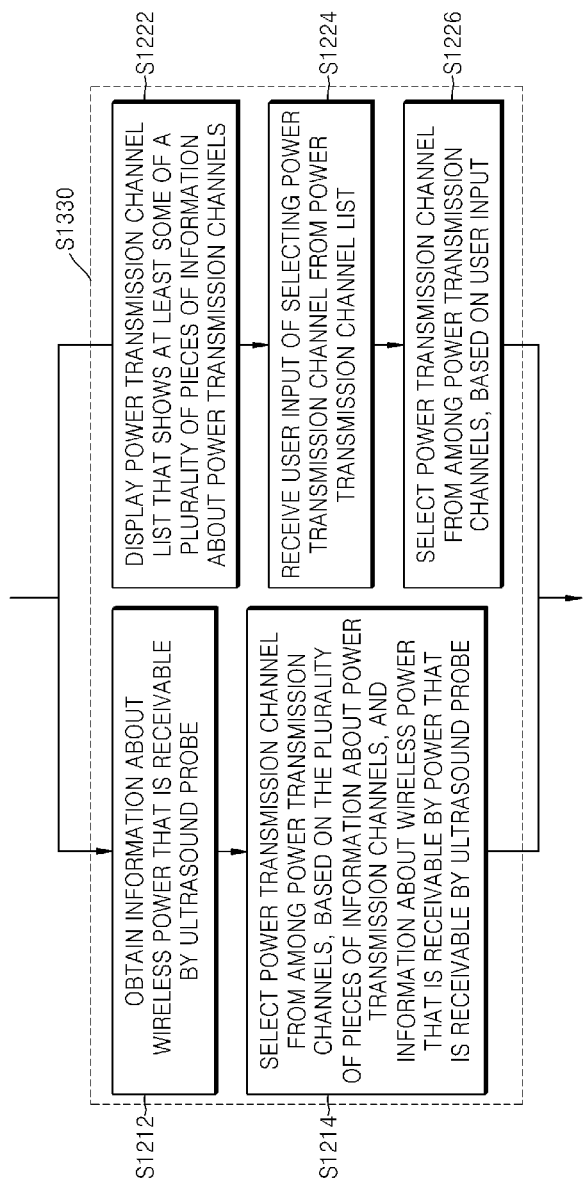
FIG. 12 is a flowchart of a detailed process of selecting a wireless power transmission channel in an operating method of an ultrasound diagnosis apparatus according to an embodiment of the present invention.

FIG. 12 is a flowchart of a detailed process of selecting a power transmission channel in the operating method of the ultrasound diagnosis apparatus 1100 according to the embodiment of the present invention.

The flowchart of FIG. 12 corresponds to operation S1330 in the flowchart of FIG. 11.

According to a first embodiment of the present invention, the ultrasound diagnosis apparatus 1100 may select at least one power transmission channel, based on information about a wireless power that is receivable by the ultrasound probe 1200.

In operation S1212, the ultrasound diagnosis apparatus 1100 may obtain the information about the wireless power that is receivable by the ultrasound probe 1200.

The information about the wireless power that is receivable by the ultrasound probe 1200 may be directly transmitted by the ultrasound probe 1200 or may be pre-stored in the ultrasound diagnosis apparatus 1100.

The information about the wireless power that is receivable by the ultrasound probe 1200 may include information about a wireless power transmission mode by which the ultrasound probe 1200 receives the wireless power, or information about a characteristic value of the wireless power that is receivable by the ultrasound probe 1200.

In operation S1214, the ultrasound diagnosis apparatus 1100 may select the at least one power transmission channel from among the power transmission channels, based on the plurality of pieces of information about the power transmission channels obtained in operation S1320 of the flowchart of FIG. 11, and the information about the wireless power obtained in operation S1212.

The selected power transmission channel may be a power transmission channel that transmits the wireless power that is receivable by the ultrasound probe 1200.

According to a second embodiment of the present invention, the ultrasound diagnosis apparatus 1100 may select at least one power transmission channel from among power transmission channels, based on a user input.

In operation S1222, the ultrasound diagnosis apparatus 1100 may display a power transmission channel list that shows at least some of a plurality of pieces of information about the power transmission channels, based on the plurality of pieces of information about the power transmission channels obtained in operation S1320.

The power transmission channel list may show identifiers (e.g., a name, an allocated number, an allocated text, or an allocated symbol of each of the power transmission channels) that correspond to the power transmission channels, respectively, and the plurality of pieces of information about the power transmission channels obtained in operation S1320.

For example, the power transmission channel list may include at least one of a plurality of pieces of information about characteristic values of wireless powers that are transmittable from the power transmission channels to the ultrasound probe 1200, and a plurality of pieces of information about wireless power transmission modes by which the power transmission channels transmit the wireless powers to the ultrasound probe 1200. Each of the characteristic values of the wireless powers may be a value that indicates at least one of a voltage, a current, a power, and a frequency of each of the wireless powers.

The ultrasound diagnosis apparatus 1100 in the second embodiment may display at least some of the plurality of pieces of information about the power transmission channels on the power transmission channel list, based on priority orders of the power transmission channels.

The priority orders of the power transmission channels may be pre-stored in the ultrasound diagnosis apparatus 1100.

The ultrasound diagnosis apparatus 1100 may match the identifiers of the power transmission channels with the priority orders and store them. Thus, the ultrasound diagnosis apparatus 1100 may obtain the identifiers of the power transmission channels from the plurality of pieces of information about the power transmission channels, and may scan the pre-stored priority orders with respect to the identifiers.

Alternatively, the priority orders of the power transmission channels may be determined based on user input information.

Alternatively, the priority orders of the power transmission channels may be determined according to the plurality of pieces of information about the power transmission channels obtained in operation S1320.

For example, the ultrasound diagnosis apparatus 1100 may determine the priority orders of the power transmission channels, based on the characteristic values of the wireless powers transmitted by the power transmission channels.

In more detail, the ultrasound diagnosis apparatus 1100 may assign higher priority orders to the power transmission channels, in order of strengths of the transmitted wireless powers. Alternatively, the ultrasound diagnosis apparatus 1100 may assign higher priority orders to the power transmission channels, in order of smaller differences between each of voltage values of the wireless powers transmitted by the power transmission channels and a rated voltage value of the ultrasound probe 1200. Alternatively, the ultrasound diagnosis apparatus 1100 may assign a highest priority orders to one of the power transmission channel, wherein a frequency of a wireless power transmitted by the one power transmission channel is the most similar to a frequency that is receivable by the ultrasound probe 1200.

In operation S1224, the ultrasound diagnosis apparatus 1100 may receive a user input of selecting at least one power transmission channel from the power transmission channel list.

In operation S1226, the ultrasound diagnosis apparatus 1100 may select the at least one power transmission channel from among the power transmission channels, based on the user input of selecting the at least one power transmission channel from the power transmission channel list.

The ultrasound diagnosis apparatus 1100 in the second embodiment may provide a GUI for allowing a user to conveniently select a power transmission channel, by displaying the power transmission channel list based on the plurality of pieces of information about the power transmission channels.

Although not illustrated in FIG. 12, the ultrasound diagnosis apparatus 1100 in a third embodiment may automatically select at least one power transmission channel from among the power transmission channels, based on the priority orders of the power transmission channels.

However, the method of selecting a power transmission channel, performed by the ultrasound diagnosis apparatus 1100, is not limited to the aforementioned embodiments.

Figure 13:
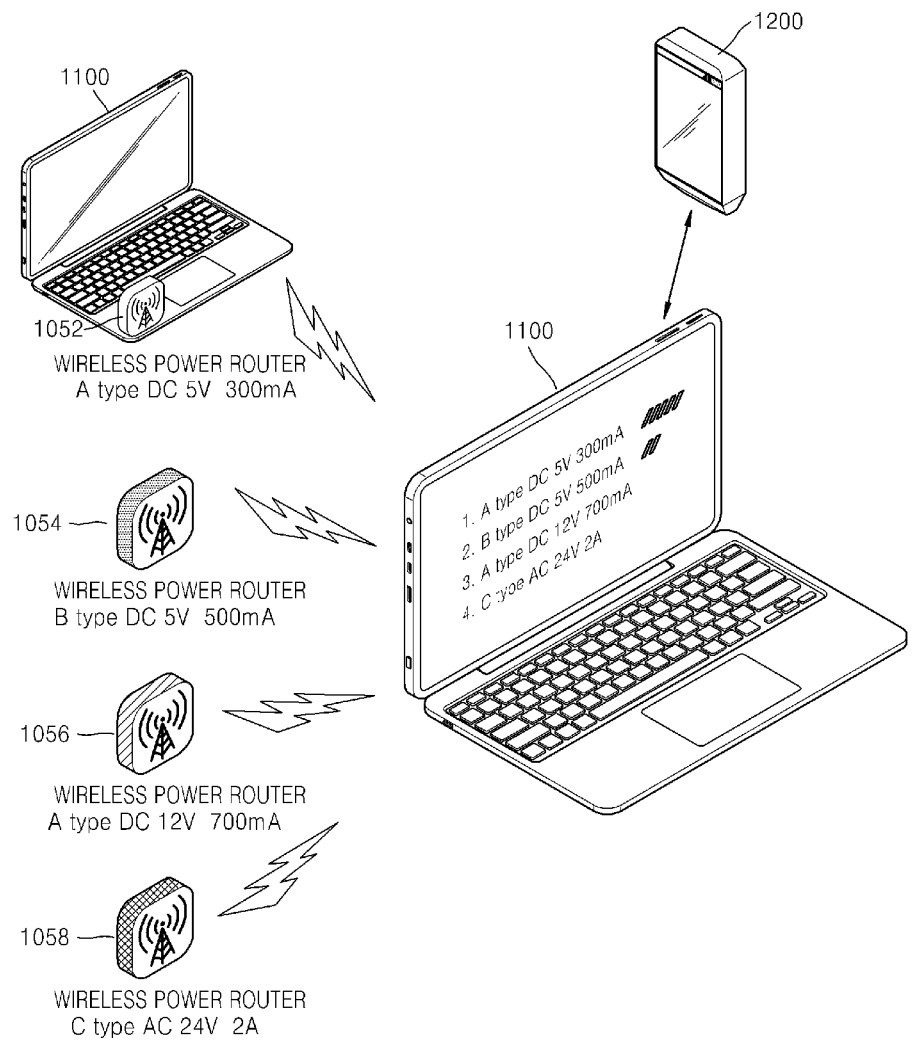
FIG. 13 illustrates an example of a screen displayed on an ultrasound diagnosis apparatus, according to an embodiment of the present invention.

FIG. 13 illustrates an example of a screen displayed on the ultrasound diagnosis apparatus 1100, according to an embodiment of the present invention.

Referring to FIG. 13, the ultrasound diagnosis apparatus 1100 and power transmission channels 1052, 1054, 1056, and 1058 exist.

As illustrated in FIG. 13, the ultrasound diagnosis apparatus 1100 may display a power transmission channel list, based on a plurality of pieces of information about the power transmission channels 1052, 1054, 1056, and 1058.

The power transmission channel list that is displayed on the ultrasound diagnosis apparatus 1100 may include wireless power transmission modes used by the power transmission channels 1052, 1054, 1056, and 1058 so as to transmit wireless powers to the ultrasound probe 1200, information about whether each of the transmitted wireless powers is alternating current (AC) or direct current (DC), a voltage and current of each of the transmitted wireless powers, and information about whether each of the transmitted wireless powers is appropriate for the ultrasound diagnosis apparatus 1100.

Referring to FIG. 13, the power transmission channel 1052 uses an A method so as to transmit a power, transmits DC, and transmits a wireless power of 5V 300 mA. The ultrasound diagnosis apparatus 1100 obtains the information about the power transmission channel 1052, and thus displays [A type DC 5V 300 mA] as illustrated in FIG. 13. The power transmission channel 1052 may be a power supply device included in the ultrasound diagnosis apparatus 1100.

The power transmission channel 1054 uses a B method so as to transmit a power, transmits DC, and transmits a wireless power of 5V 500 mA. The ultrasound diagnosis apparatus 1100 obtains the information about the power transmission channel 1054, and thus displays [B type DC 5V 500 mA] as illustrated in FIG. 13.

The power transmission channel 1056 uses an A method so as to transmit a power, transmits DC, and transmits a wireless power of 12V 700 mA. The ultrasound diagnosis apparatus 1100 obtains the information about the power transmission channel 1056, and thus displays [A type DC 12V 700 mA] as illustrated in FIG. 13.

The power transmission channel 1058 uses a C method so as to transmit a power, transmits AC, and transmits a wireless power of 24V 2A. The ultrasound diagnosis apparatus 1100 obtains the information about the power transmission channel 1058, and thus displays [C type AC 24V 2A] as illustrated in FIG. 13.

The ultrasound diagnosis apparatus 1100 may display at least some of the plurality of pieces of information about the power transmission channels 1052, 1054, 1056, and 1058 on the power transmission channel list, based on priority orders of the power transmission channels 1052, 1054, 1056, and 1058.

Hereinafter, for convenience of description, it is assumed that a rated voltage and rated current of the ultrasound probe 1200 are 10V and 1A, respectively.

The ultrasound diagnosis apparatus 1100 may obtain information indicating that the rated voltage is 10V and the rated current is 1A, from the ultrasound probe 1200 that is wirelessly connected with the ultrasound diagnosis apparatus 1100.

Since the power transmission channel 1052 and the power transmission channel 1054 satisfy the rated voltage and the rated current of the ultrasound probe 1200, the ultrasound diagnosis apparatus 1100 may determine that wireless powers transmitted by the power transmission channel 1052 and the power transmission channel 1054 are appropriate for the ultrasound probe 1200.

On the other hand, the power transmission channel 1056 and the power transmission channel 1058 do not satisfy the rated voltage and the rated current of the ultrasound probe 1200, thus, the ultrasound diagnosis apparatus 1100 may determine that wireless powers transmitted by the power transmission channel 1056 and the power transmission channel 1058 are not appropriate for the ultrasound probe 1200.

Whether a wireless power transmitted by a power transmission channel is appropriate for the ultrasound probe 1200 may be expressed by using at least one of a figure, a text, a symbol, and a color.

Referring to FIG. 13, the ultrasound diagnosis apparatus 1100 displays a figure on the power transmission channel list so as to indicate that the power transmission channel is appropriate for the ultrasound probe 1200. The ultrasound diagnosis apparatus 1100 displays "bars" on positions that correspond to the power transmission channels 1052 and 1054 that have been determined as appropriate channels.

Also, the ultrasound diagnosis apparatus 1100 may display power transmission channels according to priority orders. In the embodiment of FIG. 13, priority orders are allocated to the power transmission channels 1052, 1054, 1056, and 1058, according to strengths of the wireless powers that are transmitted by the power transmission channels 1052, 1054, 1056, and 1058.

Referring to FIG. 13, the ultrasound diagnosis apparatus 1100 may indicate the strengths of the wireless powers that are received from the power transmission channels 1052, 1054, 1056, and 1058, by using the number of bars.

Referring to FIG. 13, it is apparent to see that the power transmission channel 1052 that transmits the strongest wireless power has the highest priority order and thus is displayed on a top of the power transmission channel list.

FIG. 14 is a flowchart of an operating method of the ultrasound probe 1200, according to another embodiment of the present invention.

In operation S1410, the ultrasound probe 1200 establishes a session with the ultrasound diagnosis apparatus 1100.

In operation S1420, the ultrasound probe 1200 may receive information about a power transmission channel from the ultrasound diagnosis apparatus 1100 via the session.

The information about the power transmission channel which is transmitted from the ultrasound diagnosis apparatus 1100 to the ultrasound probe 1200 may include information to be used by the ultrasound probe 1200 so as to receive a wireless power from the power transmission channel that corresponds to the information.

For example, the information about the power transmission channel which is transmitted from the ultrasound diagnosis apparatus 1100 to the ultrasound probe 1200 may include at least one of an identifier of the power transmission channel, a characteristic value of the wireless power transmitted by the power transmission channel, and a wireless power transmission mode used by the power transmission channel so as to transmit the wireless power.

In operation S1430, the ultrasound probe 1200 may receive the wireless power from the power transmission channel that corresponds to the information received in operation S1420, by using the information about the power transmission channel which is transmitted from the ultrasound diagnosis apparatus 1100.

Figure 15B:
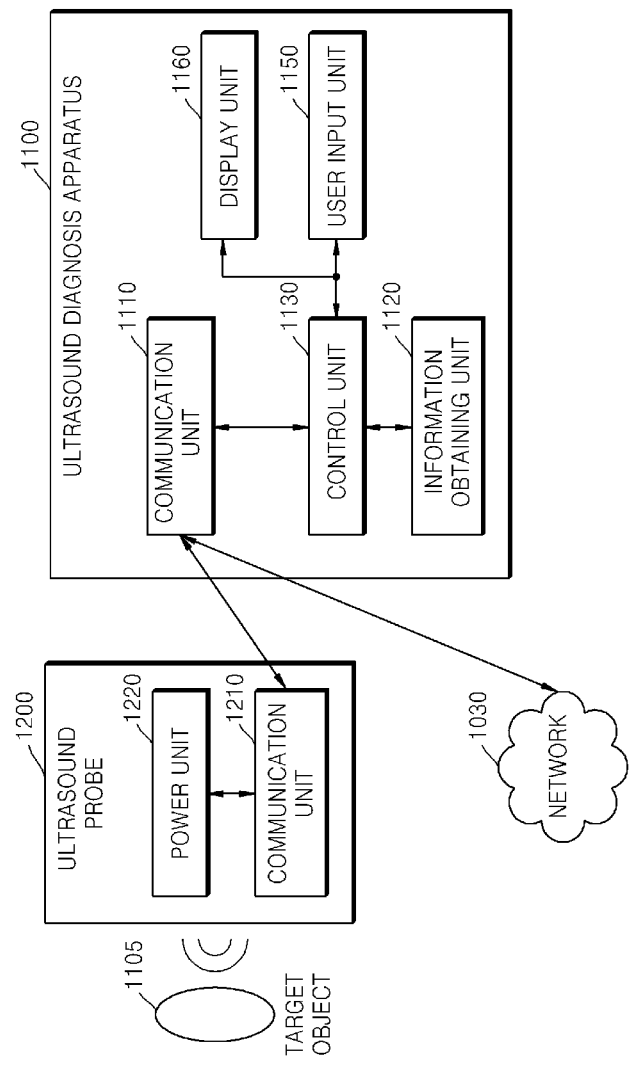

FIGS. 15A and 15B are block diagrams illustrating the ultrasound probe 1200 and the ultrasound diagnosis apparatus 1100, according to embodiments of the present invention.

Elements of the ultrasound diagnosis apparatus 1100 are configured to perform the operating method of the ultrasound diagnosis apparatus 1100 described with reference to FIG. 11. Thus, hereinafter, although descriptions are omitted, if the descriptions are related to the operating method of the ultrasound diagnosis apparatus 1100 described with reference to FIG. 11, the descriptions may also be applied to the ultrasound diagnosis apparatus 1100 shown in FIGS. 15A and 15B.

The ultrasound diagnosis apparatus 1100 shown in FIGS. 15A and 15B may completely or partially include elements of the general ultrasound diagnosis apparatus 120 shown in FIG. 1, and may perform complete or partial functions of the ultrasound diagnosis apparatus 120. Thus, hereinafter, although descriptions are omitted, if the descriptions are related to the general ultrasound diagnosis apparatus 120 shown in FIG. 1, the descriptions may also be applied to the ultrasound diagnosis apparatus 1100 shown in FIGS. 15A and 15B.

Also, elements of the ultrasound probe 1200 are configured to perform the operating method of the ultrasound probe 1200 described with reference to FIG. 14. Thus, hereinafter, although descriptions are omitted, if the descriptions are related to the operating method of the ultrasound probe 1200 described with reference to FIG. 14, the descriptions may also be applied to the ultrasound probe 1200 shown in FIGS. 15A and 15B.

In addition, the ultrasound probe 1200 shown in FIGS. 15A and 15B may completely or partially include elements of the general wireless ultrasound probe 110 shown in FIG. 1, and may perform complete or partial functions of the wireless ultrasound probe 110. Thus, hereinafter, although descriptions are omitted, if the descriptions are related to the general wireless ultrasound probe 110 shown in FIG. 1, the descriptions may also be applied to the ultrasound probe 1200 shown in FIGS. 15A and 15B.

FIG. 15A is a block diagram illustrating the ultrasound probe 1200 and the ultrasound diagnosis apparatus 1100, according to an embodiment of the present invention.

Referring to FIG. 15A, the ultrasound diagnosis apparatus 1100 may include a communication unit 1110, an information obtaining unit 1120, and a control unit 1130.

The communication unit 1110 may establish a session with the ultrasound probe 1200.

The communication unit 1110 may transmit a control signal for controlling the ultrasound probe 1200 to generate ultrasound image data, to the ultrasound probe 1200 via the session. The communication unit 1110 may receive the ultrasound image data from the ultrasound probe 1200.

The communication unit 1110 may transmit, to the ultrasound probe 1200, information about a power transmission channel selected by the control unit 1130.

The information obtaining unit 1120 may obtain a plurality of pieces of information about power transmission channels.

The control unit 1130 may select at least one power transmission channel from among the power transmission channels, based on the plurality of pieces of information about the power transmission channels obtained by the information obtaining unit 1120.

The ultrasound probe 1200 may include a communication unit 1210 and a power unit 1220.

The communication unit 1210 may establish the session with the ultrasound diagnosis apparatus 1100.

The communication unit 1210 may transmit an ultrasound signal to a target object 1105, in response to the control signal received via the session, and may generate the ultrasound image data based on the ultrasound signal reflected from the target object 1105. The communication unit 1210 may transmit the ultrasound image data to the ultrasound diagnosis apparatus 1100 via the session.

The power unit 1220 may receive a wireless power from the power transmission channel that corresponds to the information about the power transmission channel, by using the information about the power transmission channel received from the ultrasound diagnosis apparatus 1100.

The power unit 1220 may supply the wireless power to the communication unit 1210, and may supply the wireless power to be used by the ultrasound probe 1200 so as to generate the ultrasound image data.

The power unit 1220 may convert the wireless power to be appropriate for a supply to each of the elements included in the ultrasound probe 1200. That is, the power unit 1220 may convert the wireless power to be equal to or less than a rated voltage and rated current of the ultrasound probe 1200. For example, the power unit 1220 may convert the wireless power by using an SMPS, a boosting device, and/or a voltage down converter.

The power unit 1220 may include a battery that is charged with the wireless power from the power transmission channel. The power unit 1220 may include a main battery (not shown) for supplying a power to be used by the ultrasound probe 1200 in generating and transmitting the ultrasound image data to an outer source, and an auxiliary battery (not shown) for supplying a power for a standby mode or a boot-up operation of the ultrasound probe 1200.

FIG. 15B is a block diagram illustrating the ultrasound diagnosis apparatus 1100 and the ultrasound probe 1200, according to another embodiment of the present invention.

Referring to FIG. 15B, the ultrasound diagnosis apparatus 1100 may further include a user input unit 1150 and a display unit 1160.

The user input unit 1150 may receive a user input of selecting a power transmission channel from a power transmission channel list that is displayed on the display unit 1160. The user input unit 1150 may select at least one power transmission channel from among power transmission channels, based on the user input received via the user input unit 1150.

The display unit 1160 may display the power transmission channel list that shows at least some of a plurality of pieces of information about the power transmission channels, based on the plurality of pieces of information about the power transmission channels obtained by the information obtaining unit 1120.

Figure 16:
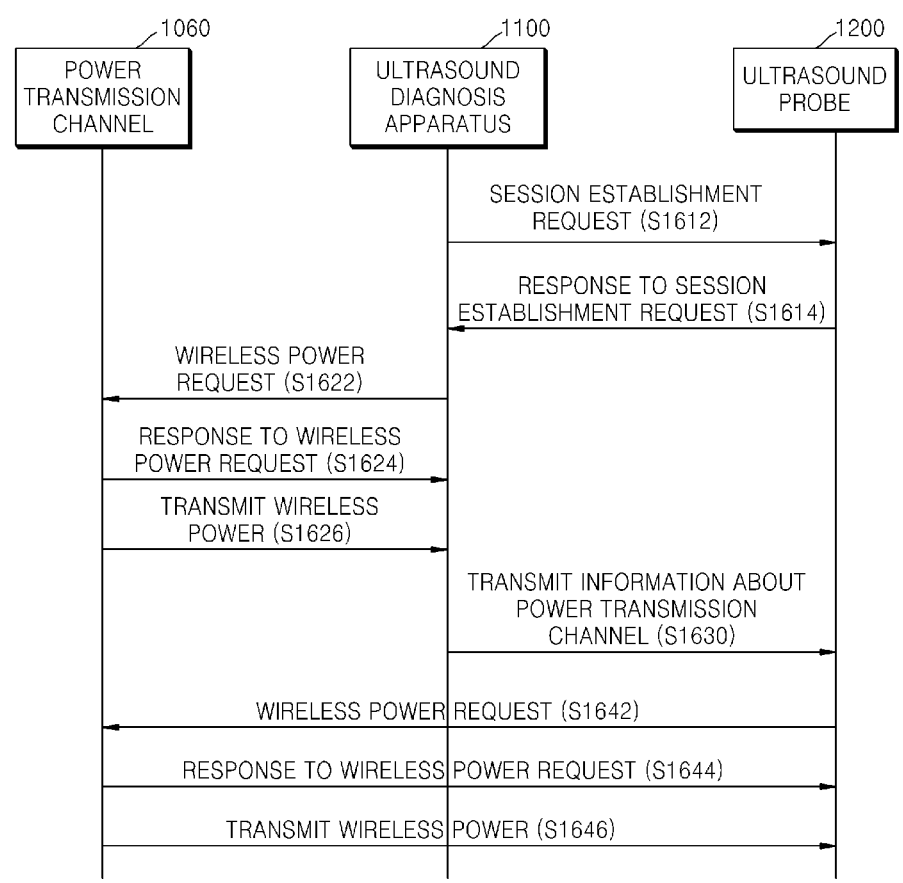
FIG. 16 is a flowchart of a procedure in which an ultrasound probe receives a wireless power by using information about a power transmission channel which is received from an ultrasound diagnosis apparatus, according to an embodiment of the present invention.

FIG. 16 is a signal flowchart of a procedure in which the ultrasound probe 1200 receives a wireless power by using information about a power transmission channel which is received from the ultrasound diagnosis apparatus 1100, according to an embodiment of the present invention.

In the embodiment of FIG. 16, in the case where the ultrasound diagnosis apparatus 1100 receives a wireless power from a power transmission channel 1060, the ultrasound diagnosis apparatus 1100 transmits information about the power transmission channel 1060 to the ultrasound probe 1200, but one or more embodiments of the present invention are not limited thereto.

In operation S1612, the ultrasound diagnosis apparatus 1100 may transmit a session establishment request to the ultrasound probe 1200. In operation S1614, the ultrasound probe 1200 may respond to the session establishment request transmitted from the ultrasound diagnosis apparatus 1100.

In contrast with the embodiment of FIG. 16, the ultrasound probe 1200 may transmit a session establishment request to the ultrasound diagnosis apparatus 1100, and the ultrasound diagnosis apparatus 1100 may respond to the session establishment request transmitted from the ultrasound probe 1200.

The ultrasound diagnosis apparatus 1100 and the ultrasound probe 1200 may recognize each other via a process of transmitting and responding to the session establishment request. Through operations S1612 and S1614, a session is established between the ultrasound diagnosis apparatus 1100 and the ultrasound probe 1200. When the session is established, the ultrasound probe 1200 may be temporarily subordinate to the ultrasound diagnosis apparatus 1100.

In operation S1622, the ultrasound diagnosis apparatus 1100 may transmit a wireless power request to the power transmission channel 1060. Here, data of the wireless power request from the ultrasound diagnosis apparatus 1100 may include information about a protocol or synchronization for an exchange of the wireless power.

In operation S1624, the ultrasound diagnosis apparatus 1100 may receive a response to the wireless power request from the power transmission channel 1060. Here, the response to the wireless power request from the power transmission channel 1060 may include the information about the protocol or the synchronization for the exchange of the wireless power.

In operation S1626, the power transmission channel 1060 may transmit the wireless power to the ultrasound diagnosis apparatus 1100.

In operation S1630, the ultrasound diagnosis apparatus 1100 may transmit information about the power transmission channel 1060 that transmits the wireless power to the ultrasound diagnosis apparatus 1100, to the ultrasound probe 1200 via the session.

In operation S1642, the ultrasound probe 1200 may transmit a wireless power request to the power transmission channel 1060, by using the information about the power transmission channel 1060 received from the ultrasound diagnosis apparatus 1100. Here, data of the wireless power request from the ultrasound probe 1200 may include the information about the protocol or the synchronization for the exchange of the wireless power.

In operation S1644, the power transmission channel 1060 may transmit a response to the wireless power request from the ultrasound probe 1200. Here, the response from the power transmission channel 1060 with respect to the wireless power request may include the information about the protocol or the synchronization for the exchange of the wireless power.

In operation S1646, the power transmission channel 1060 may transmit the wireless power to the ultrasound probe 1200.

In the embodiment shown in FIG. 16, the ultrasound diagnosis apparatus 1100 may receive the wireless power from the power transmission channel 1060 and may control the ultrasound probe 1200 to also receive the wireless power from the power transmission channel 1060.

According to the one or more embodiments of the present invention, the ultrasound probe may select a power transmission channel that is most appropriate to stably drive the wireless ultrasound probe and that is from among the plurality of power transmission channels.

Also, according to the one or more embodiments of the present invention, the ultrasound probe may efficiently deliver user-required information to a user and may allow the user to rapidly and correctly recognize information about the plurality of power transmission channels by displaying the information about the plurality of power transmission channels that wirelessly supply a power.

Also, according to the one or more embodiments of the present invention, without a separate user input of selecting the power transmission channel from which the ultrasound probe receives the wireless power, the ultrasound probe may receive the wireless power from the power transmission channel that corresponds to the information received from the ultrasound diagnosis apparatus, so that user inconvenience is decreased.

In addition, according to the one or more embodiments of the present invention, a user who uses the ultrasound diagnosis apparatus may simultaneously charge the ultrasound probe while the user charges the ultrasound diagnosis apparatus, so that user inconvenience caused by separately charging the ultrasound probe is decreased.

The one or more embodiments of the present invention may be embodied as a recording medium, e.g., a program module to be executed in computers, which include computer-readable commands. The computer storage medium may include any usable medium that may be accessed by computers, volatile and non-volatile medium, and detachable and non-detachable medium. Also, the computer storage medium may include a computer storage medium and a communication medium. The computer storage medium includes all of volatile and non-volatile medium, and detachable and non-detachable medium which are designed to store information including computer readable commands, data structures, program modules or other data. The communication medium includes computer-readable commands, a data structure, a program module, and other transmission mechanism, and includes other information transmission mediums.

The present invention may, however, be embodied in many different forms and should not be construed as being limited to the embodiments set forth herein; rather, these embodiments are provided so that this disclosure will be thorough and complete, and will fully convey the inventive concept to those of ordinary skill in the art. For example, configuring elements that are singular forms may be executed in a distributed fashion, and also, configuring elements that are distributed may be combined and then executed.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An operating method of an ultrasound diagnosis apparatus, the operating method comprising:
   establishing a session with an ultrasound probe;
   obtaining a plurality of pieces of information about each of wireless power transmission channels, wherein the plurality of pieces of information includes a wireless power transmission mode for transmitting a wireless power to the ultrasound probe at each of the wireless power transmission channels, and a characteristic value of the wireless power transmitted to the ultrasound probe by the wireless power transmission mode based on each of the wireless power transmission channels;
   selecting a wireless power transmission channel from among the wireless power transmission channels, based on the plurality of pieces of information about the wireless power transmission channels; and
   transmitting information about the wireless power transmission channel selected from among the wireless power transmission channels to the ultrasound probe via the session.

2. The operating method of claim 1, wherein the information about the wireless power transmission channel selected from among the wireless power transmission channels comprises information to be used by the ultrasound probe so as to receive a wireless power from the wireless power transmission channel selected from among the wireless power transmission channels.

3. The operating method of claim 1, wherein the information about the wireless power transmission channel selected from among the wireless power transmission channels comprises at least one of an identifier of the wireless power transmission channel selected from among the wireless power transmission channels, a characteristic value of a wireless power transmitted by the wireless power transmission channel selected from among the wireless power transmission channels, and a wireless power transmission method used by the wireless power transmission channel selected from among the wireless power transmission channels so as to transmit the wireless power.

4. The operating method of claim 1, wherein the information about the wireless power transmission channel selected from among the wireless power transmission channels is transmitted to the ultrasound probe when the ultrasound diagnosis apparatus is booted up or starts receiving a wireless power from the wireless power transmission channel selected from among the wireless power transmission channels.

5. The operating method of claim 1, wherein the transmitting of the information comprises:
obtaining information about a remaining power of a battery of the ultrasound probe; and
when a value of the remaining power is equal to or less than a predetermined value, transmitting a control signal to the ultrasound probe so as to control the ultrasound probe to receive a wireless power from the wireless power transmission channel selected from among the wireless power transmission channels.

6. The operating method of claim 1, wherein the selecting of the wireless power transmission channel comprises:
obtaining information about a wireless power that is receivable by the ultrasound probe; and
selecting the wireless power transmission channel from among the wireless power transmission channels, based on the plurality of pieces of information about the wireless power transmission channels, and the information about the wireless power that is receivable by the ultrasound probe.

7. The operating method of claim 6, wherein the information about the wireless power that is receivable by the ultrasound probe comprises at least one of information about a characteristic value of the wireless power that is receivable by the ultrasound probe, and information about a wireless power transmission method by which the ultrasound probe receives the wireless power, and
wherein the characteristic value of the wireless power indicates at least one of a voltage, a current, a power, and a frequency of the wireless power.

8. The operating method of claim 1, wherein the selecting of the wireless power transmission channel comprises selecting the wireless power transmission channel from among the wireless power transmission channels, based on priority orders of the wireless power transmission channels.

9. The operating method of claim 1, wherein the selecting of the wireless power transmission channel comprises:
displaying a wireless power transmission channel list showing at least some of the plurality of pieces of information about the wireless power transmission channels, based on the plurality of pieces of information about the wireless power transmission channels; and
selecting the wireless power transmission channel, based on a user input of selecting the wireless power transmission channel from the wireless power transmission channel list.

10. The operating method of claim 9, wherein the wireless power transmission channel list comprises at least one of a plurality of pieces of information about characteristic values of wireless powers that are transmittable from the wireless power transmission channels to the ultrasound probe, and a plurality of pieces of information about wireless power transmission methods by which the wireless power transmission channels transmit the wireless powers to the ultrasound probe, and
wherein each of the characteristic values of the wireless powers indicates at least one of a voltage, a current, a power, and a frequency of each of the wireless powers.

11. A non-transitory computer-readable recording medium having recorded thereon a program for executing the operating method of claim 1, by using a computer.

12. An ultrasound diagnosis apparatus comprising:
a communication unit for establishing a session with an ultrasound probe;
an information obtaining unit for obtaining a plurality of pieces of information about each of wireless power transmission channels, wherein the plurality of pieces of information includes a wireless power transmission mode for transmitting a wireless power to the ultrasound probe at each of the wireless power transmission channels, and a characteristic value of the wireless power transmitted to the ultrasound probe by the wireless power transmission mode based on each of the wireless power transmission channels; and
a control unit for selecting a wireless power transmission channel from among the wireless power transmission channels, based on the plurality of pieces of information about the wireless power transmission channels,
wherein the communication unit transmits information about the wireless power transmission channel selected by the control unit to the ultrasound probe via the session.

13. The ultrasound diagnosis apparatus of claim 12, wherein the information about the wireless power transmission channel selected by the control unit comprises information to be used by the ultrasound probe so as to receive a wireless power from the wireless power transmission channel selected by the control unit.

14. The ultrasound diagnosis apparatus of claim 12, wherein the information about the wireless power transmission channel selected by the control unit comprises at least one of an identifier of the wireless power transmission channel selected by the control unit, a characteristic value of a wireless power transmitted by the wireless power transmission channel selected by the control unit, and a wireless power transmission method used by the wireless power transmission channel selected by the control unit so as to transmit the wireless power.

15. The ultrasound diagnosis apparatus of claim 12, wherein the information obtaining unit further obtains information about a remaining power of a battery of the ultrasound probe, and
wherein, when a value of the remaining power is equal to or less than a predetermined value, the control unit transmits a control signal to the ultrasound probe so as to control the ultrasound probe to receive a wireless power from the wireless power transmission channel selected by the control unit.

16. The ultrasound diagnosis apparatus of claim 12, wherein the information obtaining unit further obtains information about a wireless power that is receivable by the ultrasound probe, and
wherein the control unit selects the wireless power transmission channel from among the wireless power transmission channels, based on the plurality of pieces of information about the wireless power transmission channels, and the information about the wireless power that is receivable by the ultrasound probe.

17. The ultrasound diagnosis apparatus of claim 16, wherein the information about the wireless power that is receivable by the ultrasound probe comprises at least one of information about a characteristic value of the wireless power that is receivable by the ultrasound probe, and information about a wireless power transmission mode by which the ultrasound probe receives the wireless power, and
 wherein the characteristic value of the wireless power indicates at least one of a voltage, a current, a power, and a frequency of the wireless power.

18. The ultrasound diagnosis apparatus of claim 12, wherein the control unit selects the wireless power transmission channel from among the wireless power transmission channels, based on priority orders of the wireless power transmission channels.

19. The ultrasound diagnosis apparatus of claim 12, further comprising:
 a display unit for displaying a wireless power transmission channel list showing at least some of the plurality of pieces of information about the wireless power transmission channels, based on the plurality of pieces of information about the wireless power transmission channels; and
 a user input unit for receiving a user input of selecting the wireless power transmission channel from the wireless power transmission channel list,
 wherein the control unit selects the wireless power transmission channel, based on the user input.

20. The ultrasound diagnosis apparatus of claim 19, wherein the wireless power transmission channel list comprises at least one of a plurality of pieces of information about characteristic values of wireless powers that are transmittable from the wireless power transmission channels to the ultrasound probe, and a plurality of pieces of information about wireless power transmission methods by which the wireless power transmission channels transmit the wireless powers to the ultrasound probe, and
 wherein each of the characteristic values of the wireless powers indicates at least one of a voltage, a current, a power, and a frequency of each of the wireless powers.

21. The ultrasound diagnosis apparatus of claim 12, wherein the information about the wireless power transmission channel selected by the control unit is transmitted to the ultrasound probe when the ultrasound diagnosis apparatus is booted up or starts receiving a wireless power from the wireless power transmission channel selected by the control unit.

\* \* \* \* \*